United States Patent
Quinn

(10) Patent No.: US 10,997,870 B2
(45) Date of Patent: May 4, 2021

(54) MONITORING AND ASSESSING SUBJECT RESPONSE TO PROGRAMMED PHYSICAL TRAINING

(71) Applicant: Pilates Metrics, Inc., Modesto, CA (US)

(72) Inventor: Joseph R. Quinn, Modesto, CA (US)

(73) Assignee: PILATES METRICS, INC., Modesto, CA (US)

( * ) Notice: Subject to any disclaimer, the term of this patent is extended or adjusted under 35 U.S.C. 154(b) by 572 days.

(21) Appl. No.: 15/177,240

(22) Filed: Jun. 8, 2016

(65) Prior Publication Data

US 2017/0282014 A1   Oct. 5, 2017

Related U.S. Application Data

(60) Provisional application No. 62/172,477, filed on Jun. 8, 2015.

(51) Int. Cl.
*G09B 19/00*   (2006.01)
*G06F 16/248*   (2019.01)
(Continued)

(52) U.S. Cl.
CPC ....... *G09B 19/0038* (2013.01); *G06F 3/0483* (2013.01); *G06F 3/04886* (2013.01); *G06F 16/22* (2019.01); *G06F 16/248* (2019.01); *G06F 16/24553* (2019.01); *G06F 40/186* (2020.01); *G06Q 10/1093* (2013.01); *G09B 5/14* (2013.01);
(Continued)

(58) Field of Classification Search
CPC .................................................. G09B 19/0038
See application file for complete search history.

(56) References Cited

U.S. PATENT DOCUMENTS 6,804,664 B1   10/2004  Hartman et al.
6,971,972 B1 *  12/2005  McGovern ............. G16H 20/30
                                                              482/3
(Continued)

OTHER PUBLICATIONS

User's Manual, Pro-Form 505 CST treadmill, @2010 ICON IP, Inc., pp. 5, 14-17 (Year: 2010).*

*Primary Examiner* — Xuan M Thai
*Assistant Examiner* — Sadaruz Zaman
(74) *Attorney, Agent, or Firm* — Law Office of Christopher Peil; Christopher Peil

(57) ABSTRACT

In a system for monitoring and assessing subject response to programmed physical training, a client application provides an intake form, into which subject information, such as contact information, demographics and history may be entered. At least part of the subject information may be stored in a central repository for aggregation with other subject data, for analysis and reporting. Parameterized descriptions of exercises produce a binary string for each exercise, the resulting in a binary map of an entire exercise system, such as the PILATES system. Using a digital session planner, a practitioner selects from filtered lists of exercises to generate a customized exercise sequence for a subject. After the training session, the binary strings for the session are aggregated and a summary of the session displayed for user and/or practitioner. Session data may be uploaded to the repository for aggregation with data from other subjects/session for analysis and reporting.

20 Claims, 24 Drawing Sheets

Patty Parrot
PattyParrot@gmail.com
(123) 456-789
San Francisco, CA

LEVEL
Intermediate  ⊘⊘⊘○○

TOP 5 WIP
Hundred
Roll-Up
Roll-Over
Leg Circles
Clamshells

GOALS
Tone up abs, build strength in upper body, lose excess weight around mid section.

Edit Info ⟋820

Patty knows 320 of 600 total exercises

| Exercises | Last | Times | Gap |
|---|---|---|---|
| Diaphragm Breathing | Nov 1,2015 | 10 | 10 |
| Lateral Breathing | Oct 2,2015 | 12 | 12 |
| One Lung Breathing | Sept 3,2015 | 13 | 0 |
| Sniffing Breath | Nov 1,2015 | 50 | 12 |
| Fingertip Abs/Scoop | Oct 2,2015 | 13 | 30 |
| All Fours Abdominals | Sept 3,2015 | 40 | 4 |
| Pelvic Floor | Nov 1,2015 | 22 | 01 |
| Standing Multifidi | Oct 2,2015 | 13 | 02 |
| Neutral Spine | Sept 3,2015 | 13 | 30 |
| Pelvic Clock | Nov 1,2015 | 4 | 10 |
| Imprint | Oct 2,2015 | 12 | 28 |
| Ab Curls | Sept 3,2015 | 3 | 17 |
| Oblique Curls/Crunches | Nov 1,2015 | 14 | 19 |
| Marching/Knee Folds | Oct 2,2015 | 12 | 82 |
| Toe Taps | Sept 3,2015 | 3 | 71 |
| Heel Taps | Nov 1,2015 | 45 | 83 |
| Opposite Arm and Leg Reach | Oct 2,2015 | 34 | 74 |
| Cat/ Camel | Sept 3,2015 | 34 | 98 |
| Hip Circles/Poodle Tail | Nov 1,2015 | 56 | 82 |
| Tail Wag | Oct 2,2015 | 6 | 37 |

804 STATS   806 REPITOIRE   808 SESSIONS   810 PROFILE   812 NOTES

(51) Int. Cl.

| | |
|---|---|
| *G06F 3/0488* | (2013.01) |
| *G06F 3/0483* | (2013.01) |
| *A63B 71/06* | (2006.01) |
| *G06F 3/0482* | (2013.01) |
| *G06F 16/22* | (2019.01) |
| *G06F 16/2455* | (2019.01) |
| *G06Q 10/10* | (2012.01) |
| *G16H 20/30* | (2018.01) |
| *G16H 40/67* | (2018.01) |
| *G06F 40/186* | (2020.01) |
| *G09B 5/14* | (2006.01) |
| *G09B 7/07* | (2006.01) |
| *G09B 7/10* | (2006.01) |
| *G16H 20/40* | (2018.01) |

(52) U.S. Cl.
CPC ............... *G09B 7/07* (2013.01); *G09B 7/10* (2013.01); *G16H 20/30* (2018.01); *G16H 20/40* (2018.01); *G16H 40/67* (2018.01); *A63B 71/0619* (2013.01); *G06F 3/0482* (2013.01)

(56) References Cited

U.S. PATENT DOCUMENTS

| | | | |
|---|---|---|---|
| 9,474,934 B1* | 10/2016 | Krueger | G09B 19/003 |
| 10,290,227 B2 | 5/2019 | Quinn | |
| 2012/0254333 A1 | 10/2012 | Chandramouli et al. | |
| 2013/0130215 A1* | 5/2013 | Bock | A61B 5/14532 |
| | | | 434/247 |
| 2013/0310221 A1* | 11/2013 | Zuber | G06F 19/3481 |
| | | | 482/8 |
| 2014/0147820 A1* | 5/2014 | Snow | G09B 19/0038 |
| | | | 434/247 |
| 2014/0174174 A1* | 6/2014 | Uehara | A61B 5/227 |
| | | | 73/379.01 |
| 2014/0330408 A1* | 11/2014 | Rolley | G06F 19/3481 |
| | | | 700/91 |
| 2015/0005911 A1* | 1/2015 | Lake, II | G06Q 50/22 |
| | | | 700/91 |
| 2015/0151161 A1* | 6/2015 | Anderton | A63B 24/0062 |
| | | | 700/91 |
| 2015/0217164 A1 | 8/2015 | Lagree | |
| 2015/0364057 A1 | 12/2015 | Catani et al. | |
| 2016/0199693 A1* | 7/2016 | Vermilyea | A61B 5/6831 |
| | | | 700/91 |

* cited by examiner

Patty Parrot

PattyParrot@gmail.com
(123) 456-789
San Francisco, CA

LEVEL
Intermediate  ●●●○○

TOP 5 WIP
Hundred
Roll-Up
Roll-Over
Leg Circles
Clamshells

GOALS
Tone up abs, build strength in upper body, lose excess weight around mid section.

✎ Edit Info

| STATS | REPITOIRE | SESSIONS | PROFILE | NOTES |

Patty knows 320 of 600 total exercises

| Exercises | Last | Times | Gap |
|---|---|---|---|
| Diaphragm Breathing | Nov 1, 2015 | 10 | 10 |
| Lateral Breathing | Oct 2, 2015 | 12 | 12 |
| One Lung Breathing | Sept 3, 2015 | 13 | 0 |
| Sniffing Breath | Nov 1, 2015 | 50 | 12 |
| Fingertip Abs/Scoop | Oct 2, 2015 | 13 | 30 |
| All Fours Abdominals | Sept 3, 2015 | 40 | 4 |
| Pelvic Floor | Nov 1, 2015 | 22 | 01 |
| Standing Multifidi | Oct 2, 2015 | 13 | 02 |
| Neutral Spine | Sept 3, 2015 | 13 | 30 |
| Pelvic Clock | Nov 1, 2015 | 4 | 10 |
| Imprint | Oct 2, 2015 | 12 | 28 |
| Ab Curls | Sept 3, 2015 | 3 | 17 |
| Oblique Curls/Crunches | Nov 1, 2015 | 14 | 19 |
| Marching/Knee Folds | Oct 2, 2015 | 12 | 82 |
| Toe Taps | Sept 3, 2015 | 3 | 71 |
| Heel Taps | Nov 1, 2015 | 45 | 83 |
| Opposite Arm and Leg Reach | Oct 2, 2015 | 34 | 74 |
| Cat/Camel | Sept 3, 2015 | 34 | 98 |
| Hip Circles/Poodle Tail | Nov 1, 2015 | 56 | 82 |
| Tail Wag | Oct 2, 2015 | 6 | 37 |

FIG. 9

802 — Patty Parrot

PattyParrot@gmail.com
(123) 456-789
San Francisco, CA

LEVEL
Intermediate ●●●○○

TOP 5 WIP
Hundred
Roll-Up
Roll-Over
Leg Circles
Clamshells

GOALS
Tone up abs, build strength in upper body, lose excess weight around mid section.

✎ Edit Info — 820

804 STATS | 806 REPITOIRE | 808 SESSIONS | 810 PROFILE | 812 NOTES

1000

NEXT

Thurs, July 16
1:00 PM-2:00 PM — Mobility training with Patty

Thurs, July 18
1:00 PM-2:00 PM — Afternoon intro session

PAST

Thurs, July 2
1:00 PM-2:00 PM — Mobility training with Sarah

Thurs, June 20
1:00 PM-2:00 PM — Afternoon intro session

Thurs, June 17
1:00 PM-2:00 PM — Mobility training with Sarah

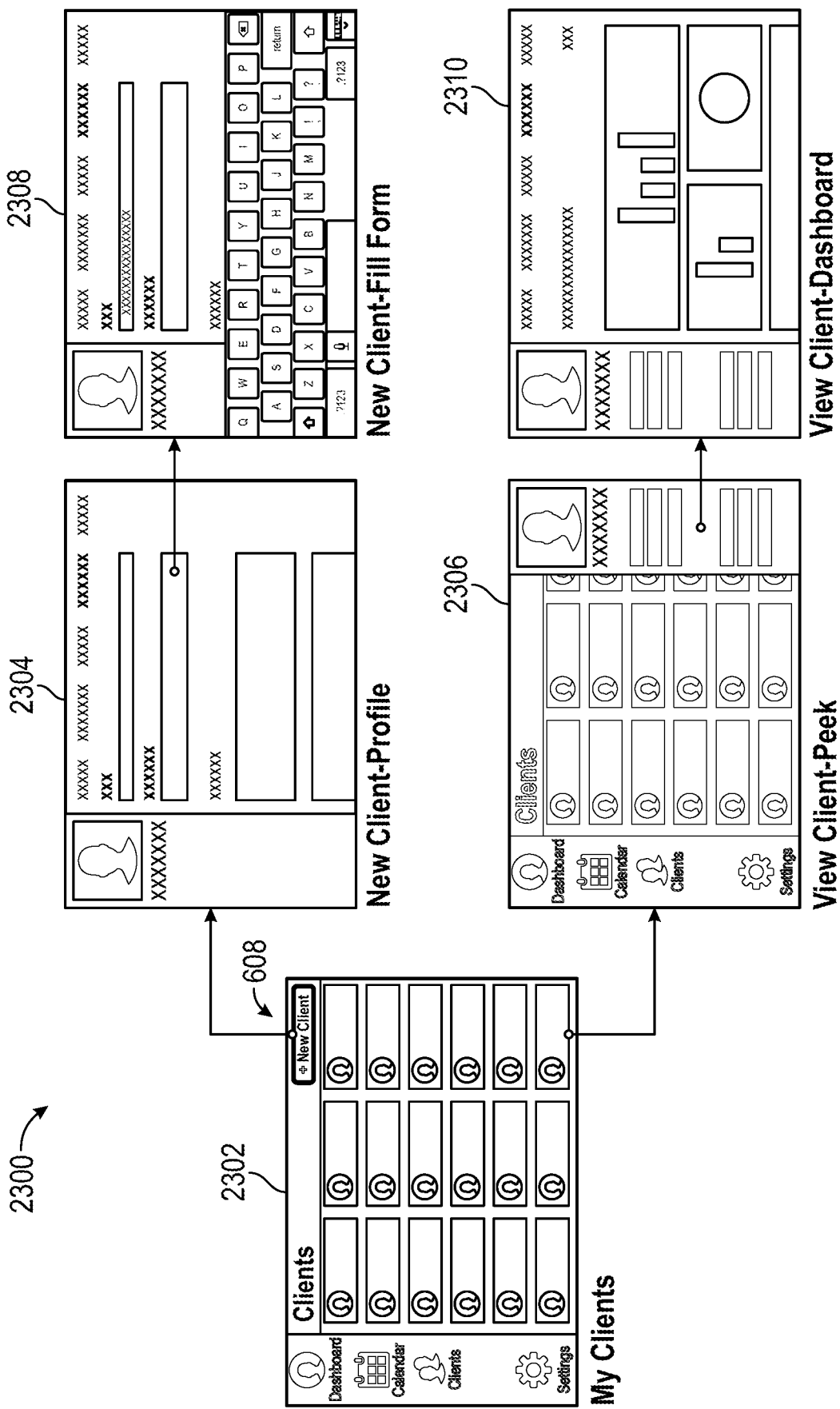

MONITORING AND ASSESSING SUBJECT RESPONSE TO PROGRAMMED PHYSICAL TRAINING

CROSS REFERENCE TO RELATED APPLICATIONS

This application claims benefit of U.S. provisional application Ser. No. 62/172,477, filed Jun. 8, 2015, the entirety of which is incorporated herein by this reference thereto.

TECHNICAL BACKGROUND

Technical Field

The present disclosure relates to programmed physical training. More particularly, the present disclosure relates to a device and method for monitoring and assessing subject response to programmed physical training.

Background Information

Among our aging and increasingly sedentary population, gentler, more mindful forms of physical training and exercise are becoming more popular. Additionally, with the time constraints within which almost everyone lives today, highly efficient forms of physical training are more and more sought after. One system of physical training that has enjoyed a huge increase in popularity is the Pilates system.

Twenty years ago Pilates was an esoteric rehabilitative strength and conditioning regimen utilized by professional modern dancers in select cosmopolitan U.S. cities. Today Pilates is a billion-dollar global industry, growing exponentially with each passing year.

Pilates' unique approach to human body development emphasizes true balance between the muscular, skeletal and joint systems. It is neither "no pain, no gain" weight training nor is it Yoga, with its emphasis on Eastern spirituality. Pilates is a system predicated on the biomechanics and anatomy of the human body. It is this logical and scientifically-reasoned approach, and its consistent returns, that has made it appealing to a broad demographic, from young professional athletes to elders who haven't exercised in decades.

The balance achieved in the body through the gentle application of Pilates has made the modality popular among those suffering various degenerative ailments: for example, sciatica and herniated discs, joint problems and bone mineral loss. Pilates is increasingly being turned to as a post-surgical rehabilitative modality, for example, for spine surgeries and joint replacements. This measured approach and the subsequent positive results have recently generated traction for Pilates in mainstream healthcare. Gradually, more and more health care providers are referring patients to Pilates practitioners and more and more insurance groups are covering it in their flexible spending plans.

Conventionally, response to exercise is fairly easy to measure. In weight lifting, an increase in weight signifies increased strength. Running is quantified in time (speed) and distance (endurance). Similar quantifiable and measurable units have been devised or found for most forms of exercise. Recently, there has been an explosion of FITBITs (FITBIT, Inc., San Francisco, Calif.) and other wearables that track and provide personal data for these endeavors. Due to the fact that Pilates encompasses diverse body mechanics, no singular unit of measurement has been found or devised to measure subject response and progress. Conventionally, subject progress is tracked with pencil and paper on a basic chart. Beginner, intermediate and advanced charts of Pilates exercises are used to denote a subject's progress. These charts accumulate at studios in file folders littered with POST-IT (3M Corporation, St. Paul, Minn.) notes. The charts tell only a small fraction of what is being accomplished and data from patron sessions is not often shared with anyone other than the patron. Leaders within the Pilates community fear that a lack of quality data, presented in accessible formats, concerning Pilates' efficacy may be hampering its further adoption in the mainstream healthcare community.

Digital fitness tracking is a behavior modification technology that has massive proven commercial appeal and untapped potential in the digital health space. To date, there has been little interest in this technology among those in the Pilates industry. Nonetheless, Goldman Sachs reports $6B of emerging commercial opportunity in the Healthcare industry for digital health solutions promoting behavioral modification. It has been proposed that the market will be won by companies that identify, motivate, and report improved client activity, thereby lowering healthcare costs.

SUMMARY

In a device for monitoring and assessing subject response to programmed physical training, a client application provides an intake form into which patron information, such as contact information, demographics and history may be entered. At least part of the subject information may be stored in a central repository for aggregation with other subject data for analysis and reporting. Parameterized descriptions of exercises produce a binary string for each exercise, resulting in a binary map of an entire exercise system, such as the PILATES system. Using a digital session planner, a practitioner selects from filtered lists of exercises to generate a customized exercise sequence for a patron. After the training session, the binary strings for the session are aggregated and a summary of the session displayed for patron and/or practitioner. Session data may be uploaded to the repository for aggregation with data from other subjects/sessions for analysis and reporting.

BRIEF DESCRIPTION OF THE DRAWINGS

FIG. 9 provides a screenshot of a 'Repertoire' page in a 'Patron Dashboard' from the GUI of FIG. 4;

FIG. 10 provides a screenshot of a 'Sessions' page in a 'Patron Dashboard' from the GUI of FIG. 4;

FIG. 16 provides a screenshot of a filled-in page in the 'Session Builder' from the GUI of FIG. 4;

FIG. 17 provides a screenshot of an 'Add Clients' page in the 'Session Builder' from the GUI of FIG. 4;

FIG. 18 provides a screenshot of a 'View Client Stub' page in the 'Session Builder' from the GUI of FIG. 4;

FIG. 19 provides a screenshot of a 'Set Date & Time' page in the 'Session Builder' from the GUI of FIG. 4;

FIGS. 20A-C provide screenshots of a 'Set Repeat' in the 'Session Builder' from the GUI of FIG. 4; and FIGS. 21-23 provide diagrams of exemplary user flows from the application of FIG. 3

DETAILED DESCRIPTION

In a device for monitoring and assessing subject response to programmed physical training, a client application provides an intake form into which subject information, such as contact information, demographics and history may be entered. At least part of the subject information may be stored in a central repository for aggregation with other subject data for analysis and reporting. Parameterized descriptions of exercises produce a binary string for each exercise, resulting in a binary map of an entire exercise system, such as the PILATES system. Using a digital session planner, a practitioner selects from filtered lists of exercises to generate a customized exercise sequence for a patron. After the training session, the binary strings for the session are aggregated and a summary of the session displayed for user and/or practitioner. Session data may be uploaded to the repository for aggregation with data from other subjects/sessions for analysis and reporting.

Figure 1:
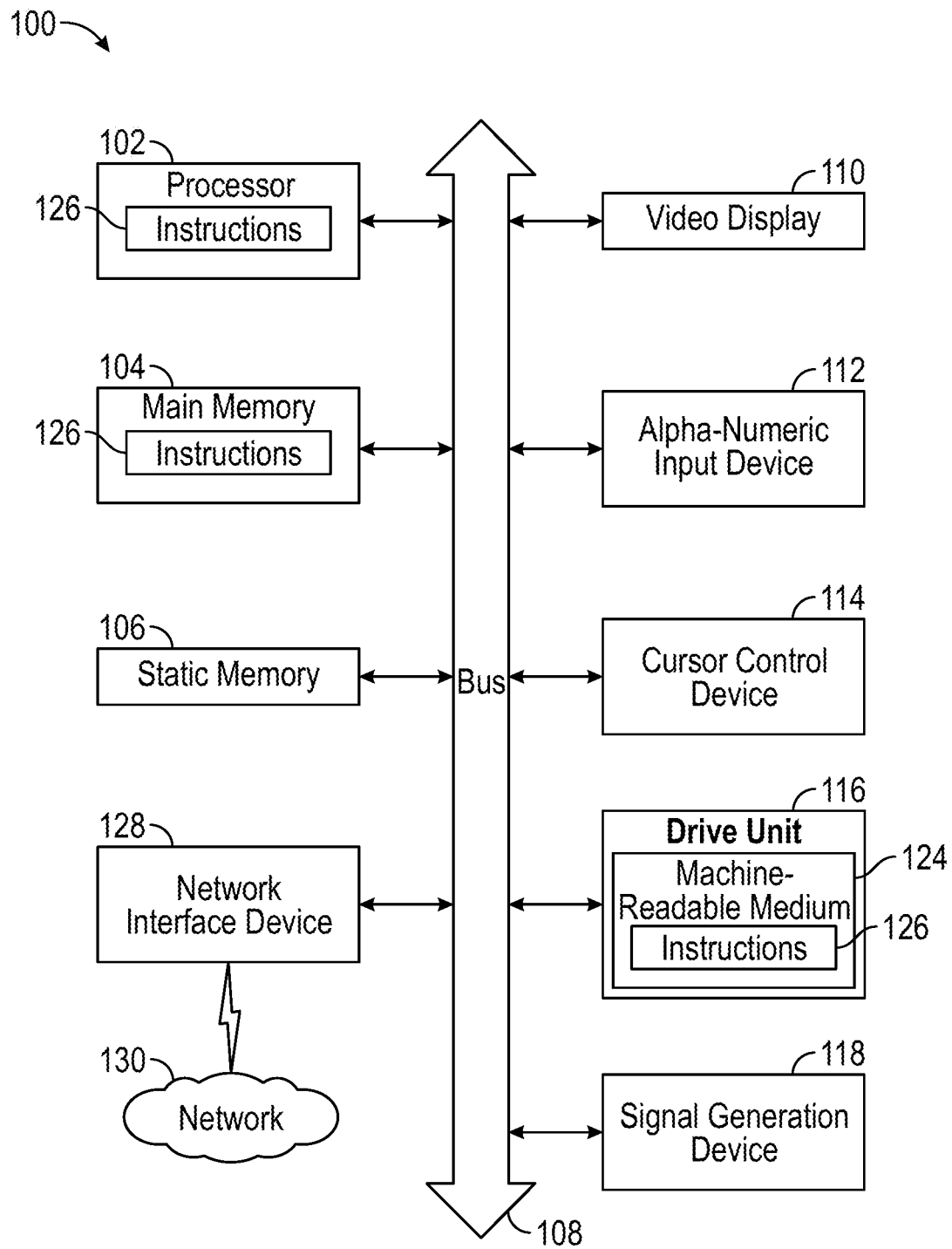
FIG. 1 provides a diagram of a machine in the exemplary form of a computer system within which a set of instructions, for causing the machine to perform any one of the methodologies discussed herein below, may be executed.

Referring now to FIG. 1, shown is a diagrammatic representation of a machine in the exemplary form of a computer system 100 within which a set of instructions for causing the machine to perform any one of the methodologies discussed herein below may be executed. In alternative embodiments, the machine may comprise a network router, a network switch, a network bridge, personal digital assistant (PDA), a cellular telephone, a web appliance or any machine capable of executing a sequence of instructions that specify actions to be taken by that machine.

The computer system 100 includes a processor 102, a main memory 104 and a static memory 106, which communicate with each other via a bus 108. The computer system 100 may further include a display unit 110, for example, a liquid crystal display (LCD) or a cathode ray tube (CRT). The computer system 100 also includes an alphanumeric input device 112, for example, a keyboard; a cursor control device 114, for example, a mouse; a disk drive unit 116, a signal generation device 118, for example, a speaker, and a network interface device 128.

The disk drive unit 116 includes a machine-readable medium 124 on which is stored a set of executable instructions, i.e. software, 126 embodying any one, or all, of the methodologies described herein below. The software 126 is also shown to reside, completely or at least partially, within the main memory 104 and/or within the processor 102. The software 126 may further be transmitted or received over a network 130 by means of a network interface device 128.

In contrast to the system 100 discussed above, an embodiment uses logic circuitry instead of computer-executed instructions to implement the functionality of a device and method for monitoring and assessing subject response to programmed physical training.

Depending upon the particular requirements of the application in the areas of speed, expense, tooling costs, and the like, this logic may be implemented by constructing an application-specific integrated circuit (ASIC) having thousands of tiny integrated transistors. Such an ASIC may be implemented with CMOS (complementary metal oxide semiconductor), TTL (transistor-transistor logic), VLSI (very large scale integration), or another suitable construction. Other alternatives include a digital signal processing chip (DSP), discrete circuitry (such as resistors, capacitors, diodes, inductors, and transistors), field programmable gate array (FPGA), programmable logic array (PLA), programmable logic device (PLD), and the like.

It is to be understood that embodiments of this invention may be used as or to support software programs executed upon some form of processing core (such as the Central Processing Unit of a computer) or otherwise implemented or realized upon or within a machine or a computer-readable medium. A machine-readable medium includes any mechanism for storing or transmitting information in a form readable by a machine, e.g. a computer. For example, a machine readable medium includes read-only memory (ROM); random access memory (RAM); magnetic disk storage media; optical storage media; flash memory devices; or any other type of media suitable for storing or transmitting information. Additionally, a "machine-readable medium" may be understood to mean a non-transitory medium. A non-transitory medium does not include a transitory, propagating signal.

Figure 2:
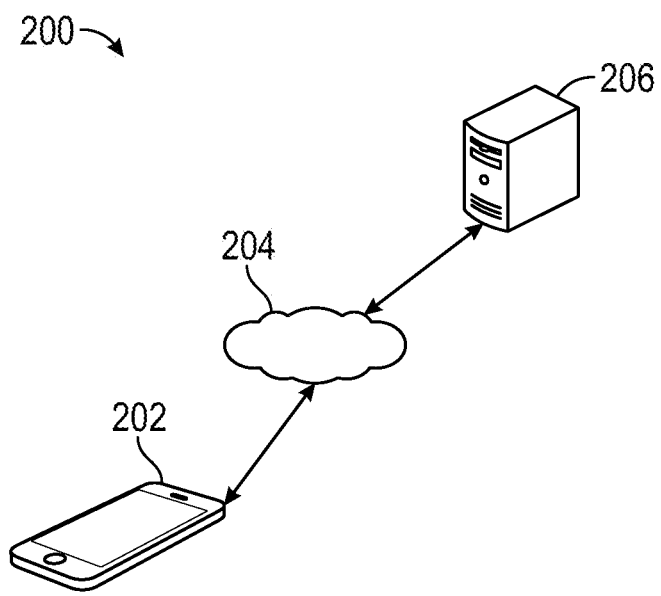
FIG. 2 provides an architecture diagram of a system for monitoring and assessing subject response to programmed physical training.

FIG. 2 provides an architecture diagram of a system 200 for monitoring and assessing subject response to programmed physical training. In an embodiment, the system may include at least a monitor 202 communicatively coupled to a server housing a remote data repository 206. In an embodiment, the server may be a virtualized server, such as found in distributed server networks of the type conventionally known as cloud-based networks. In an embodiment, the server may be a dedicated server.

In an embodiment, the monitor 202 may be a handheld mobile device such as a smartphone or a tablet computer. Mobile clients are especially suited for environments of use wherein portability/mobility is a priority. However, in environments wherein portability/mobility is of lower priority, the monitor 202 could easily be, for example, a laptop computer or even a desktop computer.

The monitor 202 and the remote data repository 206 may be connected to the network 204 via a networked data connection. Either or both of client and repository can be connected to the network via one or both of a wired and a wireless connection.

Residing on the monitor 200 is a client software application 300 that includes computer-readable instructions, which when executed by a processor, carry out a method for monitoring and assessing subject response to programmed physical training.

Figure 3:
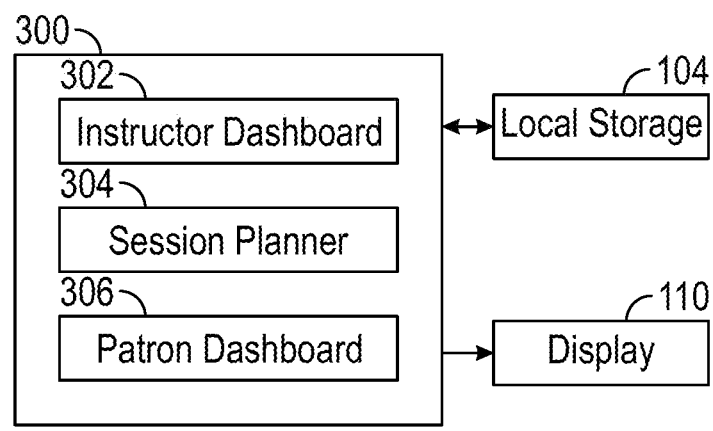
FIG. 3 provides a functional block diagram of a client application on a client device in the system of FIG. 2.

Turning now to FIG. 3, shown is a functional block diagram of the client application 300 running on the monitor 200 of FIG. 2. As shown, the client application 300 may include several modules. In an embodiment, the modules may include one or more of:

an Instructor dashboard 302;
a session planner 304; and
a patron dashboard 306.

More will be said about the individual modules herein below.

As previously described, patron and session data may be uploaded to the remote data repository, where the data may be aggregated for analysis and reporting. The client application may additionally write data to a local data store for efficient access. For example, the local data store may include a database containing patron information provided by the patron during an intake process. Additionally, the local data store may store session data for a predefined number of sessions. The number of sessions is a matter of design choice limited only by the amount of physical storage available to the client application on the client device. One or both of the remote and the local data stores may include a database containing the parameterized exercise descriptions, the binary strings and a mapping of each exercise to its binary string.

Additionally, as shown in FIG. 3, the client application may output data for display. For example, as described herein below, activating a particular UI (user interface) feature causes the application to aggregate session data and to display the aggregated data in various configurations for viewing by the patron and/or the practitioner. In an embodiment, the client application 300 may be a subscription-based application for movement professionals, such as Pilates instructors and their patrons.

Pilates Metrics Binary Algorithm

The algorithm embodies the foundational discovery upon which the system and method is based. It is the engine of the client application, representing the digitization of Pilates and similar systems of physical conditioning.

Inspiration for the discovery is provided by baseball's system of separating players by position and creating highly compartmentalized statistics for exact scenarios. Just as a second baseman cannot be effectively compared to a middle relief pitcher in baseball, it is exceedingly difficult to compare, for example, muscle recruitment around the shoulder girdle to ranges of motion within the hip, without a highly parameterized method of description.

Within the present approach, every aspect of the human body, from anatomy to biomechanics may receive its own category, or parameter. For example, hip movement during performance of an exercise can be, for example, neutral;
flexion;
extension;
external rotation;
internal rotation;
abduction;
adduction; and
explore range of motion (ROM).

Thus, there exist, for example, a number of separate sub-categories within the system to describe hip movement alone, that may be expressed as a series of attribute-value pairs:

hip movement: neutral;
hip movement: flexion;
hip movement: extension;
hip movement: external rotation;
hip movement: internal rotation;
hip movement: abduction;
hip movement: adduction; and
hip movement: explore range of motion (ROM).

For each relevant body part, for example, the torso, the pelvis, the feet, there may be corresponding categories of movement. The algorithm may also account for additional parameters such as starting position, balance, joint mobilization, stretched muscle groups, active muscle groups, and so on. The system of parameterized descriptions may thus be understood as a structured classification of the entire canon of Pilates exercises.

The algorithm may also account for Pilates-specific information such as level of difficulty and apparatus identification. In an embodiment, ninety-six discrete parameters may be used to describe an exercise. Nonetheless, systems having more or fewer parameters fall within the scope of the present description and claims.

When applying the system to the Pilates method, each of the approximately six hundred Pilates exercises have been run through the same series of binary questions for the ninety-six parameters, wherein the exercise was given a 1 for a "yes" answer and a zero for a "no" answer, thus generating a unique binary string for each exercise, representing, in effect, an exhaustive binary description for every exercise. Therefore, in the presently described system, each of the several hundred Pilates exercises may be fully described by a unique 96-bit binary string. One of ordinary skill will readily understand that the word "bit" is not used herein to describe binary digits. Rather, each bit in the 96-bit binary string represents a logical value—in this case, as previously indicated, each bit represents either a 'yes' or 'no' answer to the question of whether the exercise includes the relevant parameter. While the bit string includes 96 bits, the 96 bits may be numbered 0-95 according to the convention followed in the data processing arts.

In an embodiment, bits 0-4 may identify the level of difficulty of an exercise; bits 5-13 may identify equipment, such as an apparatus, on or with which an exercise is performed; bits 14-19 identify a starting position for the exercise; bits 20-26 identify planes of motion for the torso, bits 27-29 identify planes of motion for the pelvis; bits 30-36 identify planes of motion for the hip; bits 37-39 identify planes of motion for the foot; bits 39-43 identify planes of motion for the arms; bit 44 specifies whether the exercise involves a balance component; bits 45-51 identify the joint(s) mobilized by an exercise; bits 52-57 identify the joint(s) stabilized by an exercise; bits 58-76 identify the active muscle groups in an exercise; bits 77-92 identify the muscle groups stretched during an exercise; bit 93 specifies whether an exercise is bilateral or not; and, finally, bits 94-95 specify whether an exercise is part of the traditional or the modern Pilates canon.

The resulting data provides a complete binary map of the Pilates method. The core algorithm thus extracts biomechanics and anatomy from exercises.

The examples below illustrate how a complete description of a Pilates exercise may be encoded in a 96-bit binary string. Each example is of a well-known Pilates exercise and provides the binary string, the logical values that the binary string represents and a mapping of the binary value to the relevant parameter. It will be understood by the ordinarily-skilled practitioner that only binary values of '1' are discussed because a binary value of '0' is an indication that the parameter is not relevant to the exercise.

Example 1

Exercise: Toe Taps
Binary String:

10000100000000010000000001010010100000100000010000011111100111101000 1000000000000000000000000110.

Logical Values:
YNNNNYNNNNNNNNNYNNNNNNNNNNYNYNNYNYNNNNNNYNNNNNNYNNNNNYY YYYYNNYYYYNYNNNYNNNNNN NNNNNNNNNNNNNNNNYYN.

Description:
'1' at bit 0: Level of difficulty—fundamental;
'1' at bit 5: Apparatus used—floor mat;
'1' at bit 15: Starting position—supine;
'1' at bit 25: Torso—neutral plane of motion;
'1' at bit 27: Pelvis—neutral plane of motion;
'1' at bit 30: Hip—flexion plane of motion;
'1' at bit 32: Hip—flexion;
'1' at bit 39: Foot—flexion;
'1' at bit 46: Joint mobilized—hip;
'1' at bits 52-57: Joints stabilized—pelvis, shoulder, knee, elbow, wrist, and ankle;
'1' at bits 60-63, '1' at bit 65, at bit 69: Active muscle groups—transverse abdominis, pelvic floor, psoas, hip flexor, quadriceps, calves;
'1' at bit 93: Bilateral exercise; and
'1' at bit 94: Classical Pilates exercise.

Example #2

Exercise: Rotations
Binary String:
01000010000000001001011011110100001010101100000001110111010010101100000000000100100000110.

Logical Values:
NYNNNNYNNN NNNNNNNYNNYNYYNYYYNYNNNNNYNYNYYNYNN NNNNNYYYNYYYNYYYNYNNYNYYNYNNNNNNNNNNYNNYNNNNNYYN.

Description:
'1' at bit 1: Level of difficulty—beginner;
'1' at bit 6: Apparatus—Reformer;
'1' at bit 17: Starting position—seated;
'1' at bits 20, 22, 25, 26: Torso—planes of motion: flexion, rotation, spinal articulation, neutral;
'1' at bits 27, 28: Pelvis—planes of motion: neutral, posterior tilt;
'1' at bits 30 and 36: Hip—plane of motion: flexed, adducted;
'1' at bit 38: Foot—plane of motion: dorsiflexion;
'1' at bits 40, 42-43: Arms—planes of motion: flexion, abduction, adduction;
'1' at bits 45, 49: Joints mobilized—shoulder, knee;
'1' at bits 53-55, 57: Joints stabilized: shoulders, knees, elbows, ankles;
'1' at bits 61-63, 65, 68, 70-71 and 73: Active muscle groups—rectus abdominals, oblique abdominals, pelvic floor, the psoas, the hip flexors, quadriceps, the adductors, the latissimus dorsi, trapezius, and the deltoids;
'1' at bits 84, 87: Muscle groups stretched—calves, lumbar spine;
'1' at bit 93: Bilateral, yes; and
'1' at bit 94: Classical Pilates repertoire.

Example #3

Exercise: Thigh Stretch
Binary String:
000100010000000000100100010101011000000110001100010011011100110011100 01111011001110000000000010.

Logical Values:
NNNYNNNYNNNNNNNNNYNNYNNNYNYNYNYYNNNNNNYYNNNYYNNNYNNNYYN NYYYNNYYYNNNYYYYNYYNNYYYNNNNNNNNNNNNYN.

Description:
'1' at bit 3: Level of difficulty—advanced;
'1' at bit 7: Apparatus—Cadillac;
'1' at bit 18: Starting position—kneeling;
'1' at bit 21, 25: Torso—planes of motion: extension, neutral;
'1' at bits 27, 29: Pelvis—planes of motion: neutral, anterior tilt;
'1' at bits 31-32: Hip—plane of motion: flexion, neutral;
'1' at bit 39: Foot—lane of motion: plantar flexion;
'1' at bit 40: Arms—planes of motion: flexion;
'1' at bit 44: Balance component—yes;
'1' at bits 45 and 49: Joints mobilized—shoulder, knee;
'1' at bits 52-53, 55-57: Joints stabilized—pelvis, shoulder, elbow, wrist, ankle;
'1' at bits 60-61, 64-66, 65, 70-73 and 75-76: Active muscle groups—transverse abdominis, pelvis, gluteals, quadriceps, hamstrings, latissimus dorsi, trapezius, pectorals, deltoids, triceps and spinal extensors;
'1' at bits 79-81: Muscle groups stretched—psoas, hip flexor and quadriceps; and
'1' at bit 94: Classical Pilates repertoire.

It is to be appreciated that the system of highly-parameterized descriptions of individual movements and the use of binary strings to encode such descriptions may be applied to other systems of movement and exercise. For example, the system lends itself well to dance schools, such as classical ballet, and additionally may be applied to more conventional forms of physical exercise, such as yoga, or weight training and other forms of repetition-based exercise, wherein a single broad movement, such as the bench press, may have many variations, each constituting a distinct exercise. One of ordinary skill will recognize that the system is readily applicable to other movement disciplines such as martial arts, the FELDENKRAIS method or the ALEXANDER technique.

The system, of course, stores at least one data file containing a complete listing of the parameterized exercise descriptions; at least one data file containing a complete listing of the binary strings corresponding to the descriptions; and at least one data file mapping the descriptions to the binary strings. In embodiments, all data operations performed by the application/system may be performed using binary strings. The text-based parameterized descriptions are thus involved only in input/output operations, wherein textual data is input by a user and when textual data needs to be output to the user.

In summary then, the binary algorithm may be understood to comprise at least the following steps:
receiving an array of Boolean values, each of the array of Boolean values consisting of a value of a Boolean variable in an array of Boolean variables, the array of Boolean variables representing a template for a parameterized description of an exercise;
evaluating each of said Boolean values such that:
responsive to detection of a Boolean value='true', storing a value of '1' to a location in said memory; and responsive to detection of a Boolean value='false', storing a value of '0' to the location in said memory; wherein evaluation of said entire array of Boolean results in a string of binary values that represents a parameterized description of the exercise represented by the received array of Boolean values;

storing a list of the parameterized exercise descriptions and a mapping of each parameterized description to the corresponding binary string;

responsive to input of at least a portion of a parameterized exercise description, retrieving the mapped binary string for data operations;

responsive to an instruction to output a result of a data operation resulting in at least one binary string, retrieving the mapped, parameterized exercise description for each of the at least one resulting binary string; and displaying at least a portion of the mapped, parameterized exercise description.

User Interface

Figure 4:
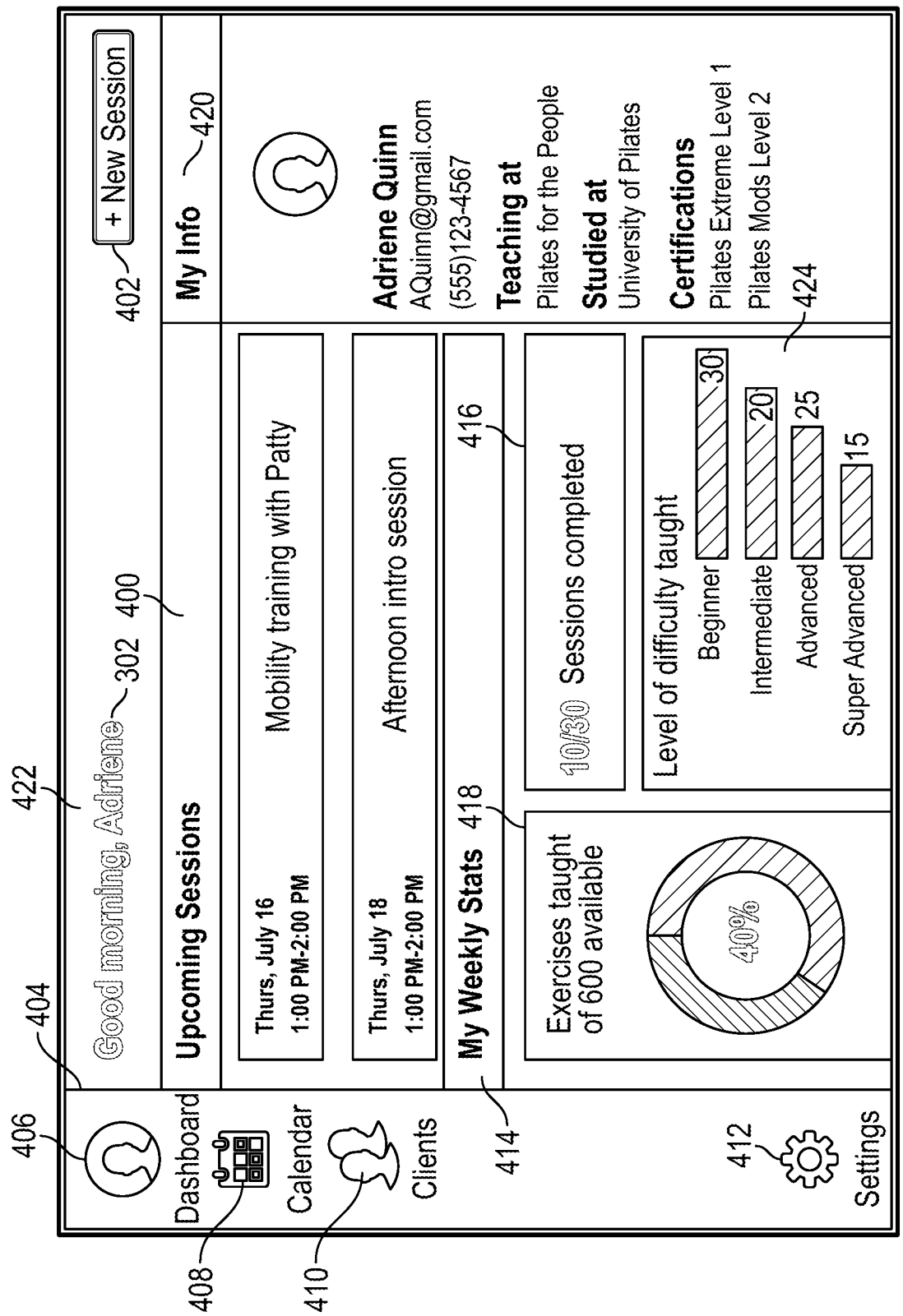
FIG. 4 provides a screenshot of an instructor dashboard in a graphical user interface (GUI) from the client device of FIG. 3.

Referring now to FIG. 4, shown is an Instructor Dashboard 302 from the GUI (graphical user interface) of the client application 300 of FIG. 3. In embodiments, the dashboard may include, for example, a personal greeting 422 to the instructor to which the particular instantiation of the Dashboard 302 is associated.

In embodiments, the Dashboard 302 may include a list 400 of the instructor's upcoming sessions. Each listing may include, for example, one or more of date, time, patron name and a brief summary of the session objective.

In embodiments, the Dashboard 302 may include a summary 414 of the instructor's statistics for a particular time period including, for example, how many sessions 416 of a total number of sessions scheduled for the particular time period have been completed, numbers of sessions taught at varying levels of difficulty 424, and the number of exercises taught out of the total number of exercises available 418 within the canon of a particular movement discipline, such as Pilates, a reflection of the instructor's level of skill.

In embodiments, the Dashboard 302 may include a summary 420 of the instructor's professional background, credentials and accomplishments, along with a certain amount of personal/biographical information.

In embodiments, the Dashboard 302 may include a menu bar 404 comprising a number of options, selection of any of which may navigate a user to additional pages within the application 300 UI. For example, as shown in FIG. 4, since the current focus is on the Dashboard 302, within the menu bar 404, a Dashboard icon 406 is highlighted. Icons for options that may be accessed from the Dashboard may remain grayed-out or otherwise obscured or subdued. In embodiments, additional options may include: a session calendar 408, a client list 410, and a 'settings' page 412.

Figure 5:
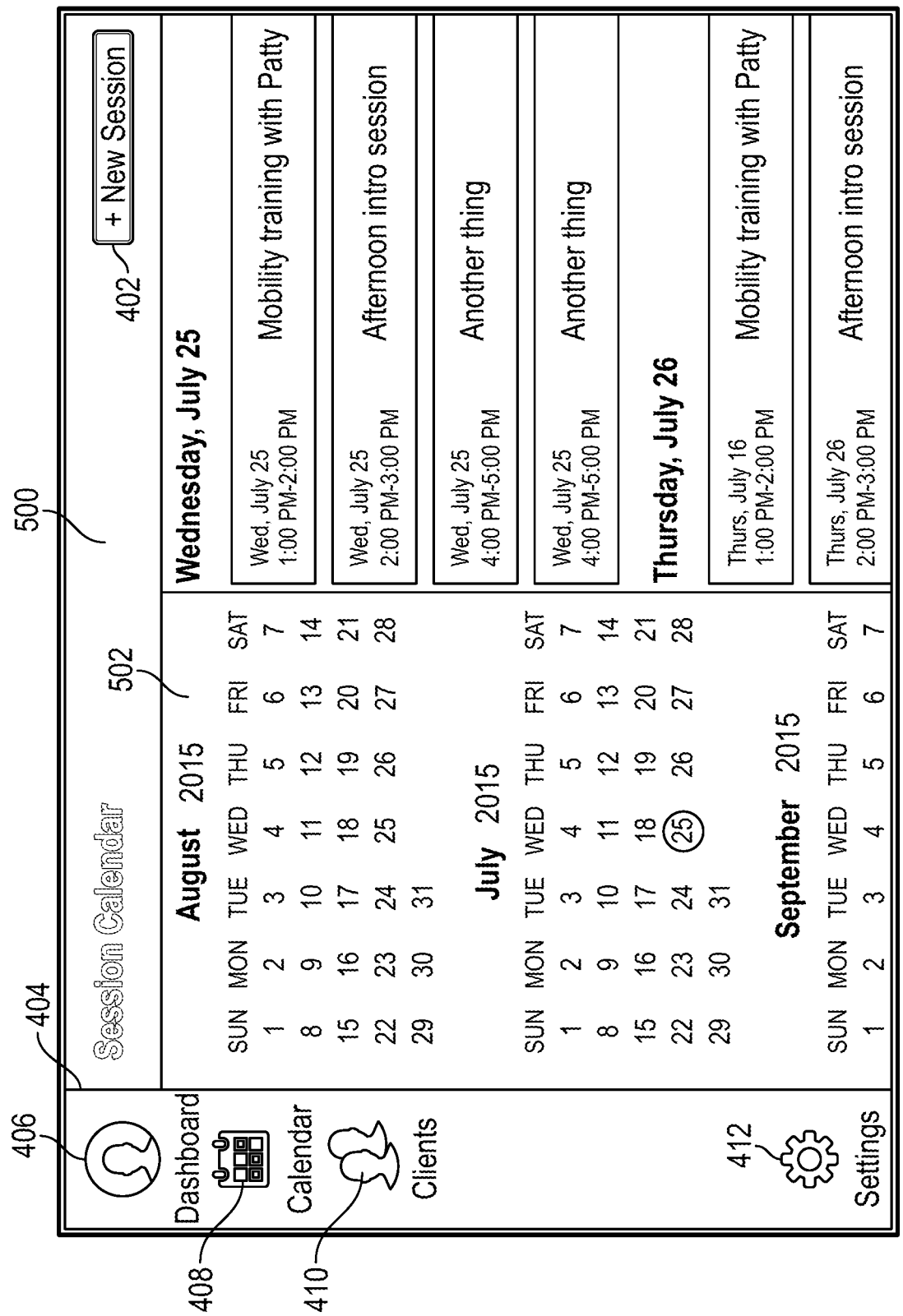
FIG. 5 provides a screenshot of a session calendar in an 'Instructor Dashboard' from the GUI of FIG. 4.

FIG. 5 shows a view of a session calendar 500, which may be accessed by selection of the session calendar icon 408 within the menu bar 404. A portion of the session calendar 500 may be occupied by calendar pages 502 for a specific time period, four weeks or three months for example. By default, the current day's date, for example, Jul. 25, 2015, is highlighted. In another portion of the session calendar, a list 400 of the instructor's upcoming sessions, at least for the current day, may be displayed.

In embodiments, an instructor may search for sessions scheduled for a particular day/date by modifying the date which currently occupies focus. The user may do this either by selecting another date using a pointing device such as a mouse, or by using keystrokes to move the focus indicator to the desired date.

It is to be appreciated that, from every page within the Dashboard 302, a user interface element 402 for creating a new session is prominently displayed and easily available.

Figure 6:
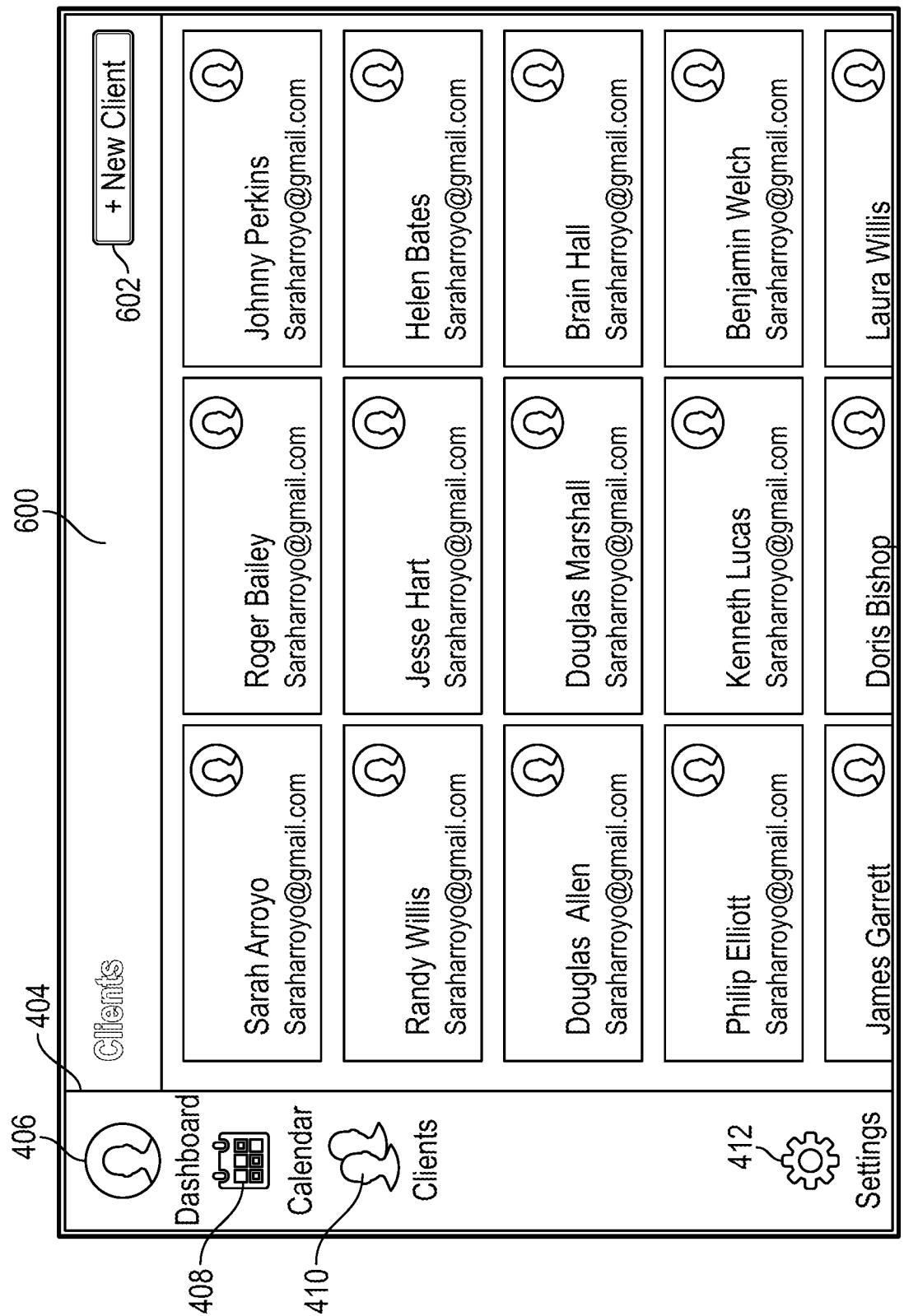
FIG. 6 provides a screenshot of a patron list in an 'Instructor Dashboard' from the GUI of FIG. 4.

FIG. 6 provides a view of a client list 600, accessible by selecting the 'clients' icon 4y0 in the menu bar 404. In embodiments, the client list 600 may display records retrieved from a client database housed on one or both of the monitor 202 and the remote server 206. As shown in FIG. 6, the client list 600 displayed, by default, includes the clients of the Instructor to which the Instructor Dashboard 302 is associated. In embodiments, the system is also capable displaying a client list associated to a group of instructors or to an entire practice entity such as studio or even a chain or studios or even a large company having many locations across the nation.

In embodiments, the UI may include a 'new client' feature 602, activation of which may present the user with a form that allows the user to create a database record for a new patron.

Figure 7:
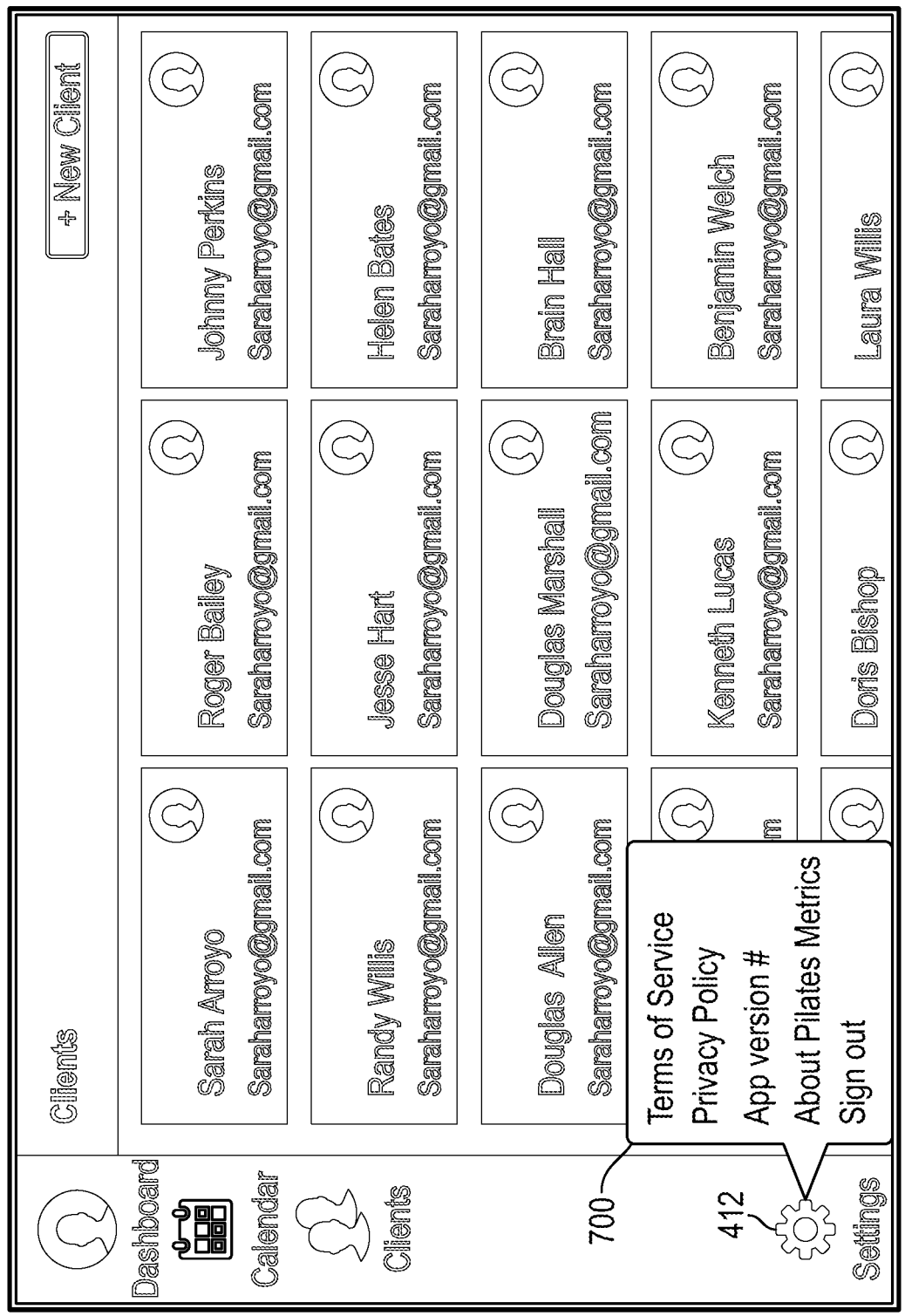
FIG. 7 provides a screenshot of a 'Settings' page in an 'Instructor Dashboard' from the GUI of FIG. 4.

Turning now to FIG. 7, shown is a 'settings' menu 700 which may be displayed upon selection of a 'settings' tab 412. In embodiments, settings may include any of:

Terms of service;

Privacy Policy;

App version #;

an "About' feature; and a 'Sign out' for logging individual users off of the application.

Figure 8:
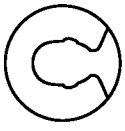
FIG. 8 provides a screenshot of a 'Patron Statistics' page in a 'Patron Dashboard' from the GUI of FIG. 4.

FIG. 8 shows a page from a Patron dashboard 304. As shown, the UI to the Patron dashboard 304 may include a number of tabs for accessing the various functionalities of the Patron dashboard 304. In embodiments, the tabs may include one or more of:

Stats 804;

Repertoire 806;

Sessions 808;

Profile 810; and

Notes 812.

Additionally, the Patron dashboard 304 may include patron-specific information 802. The patron-specific information 802 may include for example:

patron contact information such as name, email address, telephone number, residence information;

a skill level;

works-in-progress, for example a particular exercise, movement or posture with which the patron is currently engaged;

goals, such as fitness goals, performance goals, rehabilitation goals, and so on.

The patron dashboard may also include an 'edit' feature 820 to edit the patron-specific information.

Selection of the 'stats' tab 804 grants access to a 'stats' page 800. In embodiments, the 'stats' page may summarize the performance challenges a patron has been exposed to in various sessions over a particular time period. For example, the example of FIG. 8 quantifies the number of muscle groups used and/or stretched 814 during sessions over the time period. Additionally, the example provides a chart summarizing the degree of spinal articulation 816—flexion or extension of the spine a single vertebra at a time to develop and maintain spinal flexibility—required by the exercises performed by the patron during the period. Additionally, planes of motion 818 for various body parts—for example, torso, pelvis, legs, feet and arms are summarized for the period. The foregoing example is specific to the Pilates system of exercise and is not intended to be limiting. A 'stats' page can be employed to track and display any type of exercise-related statistic for any system of physical exercise: numbers of sets and reps, the amount of resistance used, yoga postures and their effects, dance movements, martial arts moves, average session length, average calories burned, maximum heart rate achieved and so on.

When an 'ENTER' button is tapped, all of the embedded data selected from the User Interface that was generated from the binary algorithm may be added downward in the respective anatomical and biomechanical categories. The results provide totals for each parameter that may then be graphed and charted and displayed on the user/patron dashboard. Each session's totals are aggregated to provide grand totals, averages, time-flow charts and so on. The visual reports allow instructors and patrons to drill down into the granular aspects of the patron's exercise session and to gain a better understanding of the patrons' bodies. In embodiments, the totals aggregate the raw movement data of the session for the various systems of the body—muscular, skeletal and joint systems, both in anatomy and biomechanics. The aggregated data further totals the exercises in level of difficulty, apparatus used, and number of bilateral and balance exercises. Each embedded exercise may be added to a "completed" list of exercises and, at the end of the session, each parameter is added down to create totals. In embodiments, the total aggregates the raw movement data of the session for the various systems of the body: muscular, skeletal and joint systems, both in anatomy and biomechanics. The application 300 also totals the exercise in level of difficulty, apparatus used, and number of bilateral and balance exercises.

Turning now to FIG. 9, shown is an example of a 'repertoire' page 900, accessed by selecting a 'repertoire' tab 806. In embodiments, the client application automatically tracks a patron's repertoire: the number of exercise he/she knows, the names of the individual exercises, how many times each exercise has been performed, the date they debuted with a particular exercise and the date the particular exercise was last performed.

As above, the example is specific to the Pilates system but is not intended to be limiting. As shown, embodiments of the 'repertoire' page 900 may provide a formatted list of the exercises the patron has mastered, the date the exercise was last performed, the total number of times the patron has performed the exercise and a time gap between sessions in which the exercise was performed. However, other types of physical skill are amenable to an organized display of the skills mastered by a patron in a 'repertoire' page 900.

In a typical scenario, over time, the totals for each of the parameters increase, reflecting the increasing volume of exercise performed by the patron, his/her increasing fitness level and exercise tolerance, a consequent improvement in the patron's health, and so on. Thus, an increase in parameter total is generally a sign of a healthy body.

Exceptions may be when a client has a pre-existing condition that would require specific session modifications. For example, a teacher trainer may have a trainee instructor, who may be preparing for certification. In the example, the trainee is working with 2 clients, one with a herniated disc and the other in her 2nd trimester of pregnancy. The teacher trainer can use the monitor to examine the teaching of the trainee. If the teacher-trainer saw that the trainee was subjecting the client having the herniated disc to too many exercises involving extension of the spine, the teacher-trainer would have the opportunity to correct the trainee because such planes of motion are dangerous to the patron. Also, if the pregnant woman displayed too many starting positions of prone exercises (lying on her stomach) it would be possible to correct the selection of exercises to minimize risk to the patron.

Therefore, while an increase in numbers generally signifies an increase in human development/performance, in specific health instances, which are frequently encountered in the fitness industry, these statistics may be monitored and used to modify activities for patrons at elevated risk.

FIG. 10 shows an example of a 'sessions' page 1000 accessed by selecting a 'sessions' tab 808. The appearance and functionality of the 'sessions' page 1000 are nearly identical to the session calendar 500 of FIG. 5, with the exception that the page code filters the session information to the patron rather than to the instructor.

Figure 11:
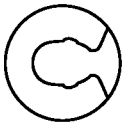
FIG. 11 provides a screenshot of a 'Profile' page in a 'Patron Dashboard' from the GUI of FIG. 4.

FIG. 11 shows an example of a 'profile' page 1100 accessed by selecting a 'profile' tab 810. In embodiments, the 'profile' page 810 provides one or more sections for entering different types of information about the patron. For example, the 'profile' page may include any of a 'bio' section 1102, a 'medical' section 1104, and a 'goals' section 1106. While, as shown in FIG. 11, the sections may constitute text fields in which narrative information may be entered, in other embodiments, each section may be an online form which specifies, in the form of questions to which the patron or instructor provides answers, exactly what information is to be provided. After the information has been provided by the patron, the data may be save to a patron database located on one or both of the local and remote servers.

In embodiments, the profile page 1100 provides a digital intake form that may gather and store patron information in at least one of the categories of:

1. Personal identifying information: name, address, phone number and email. As above, this information remains private and/or localized;
2. Vital information: sex, age, height, weight;
3. Pre-existing conditions: injuries, surgeries, medications, restrictions;
4. Movement history/activities: detailing a patron's current and past activities;
5. Goals: pain management, weight management, posture, balance, strength, flexibility; and
6. Physician and/or Physical Therapist Guidelines—targeted areas for improvement.

In embodiments, the personal identifying information may be stored and accessed according to one or more statutory privacy programs such as the HEALTH INSURANCE PORTABILITY AND ACCOUNTABILITY ACT (HIPAA) Privacy Rule or the Australian PRIVACY STATUTE.

All six categories of patron information may be stored one or both or locally and remotely. The information gathered in sub-categories 2-6 may serve as the basis for various back-end data analytics generated by the system and its users.

Figure 12:
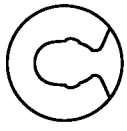
FIG. 12 provides a screenshot of a 'Notes' page in a 'Patron Dashboard' from the client GUI of FIG. 4.

In FIG. 12, an example of a 'notes' page 1200 is shown. The 'notes' page is provided to give Instructors the capability of making session notes 1202. In embodiments, the 'notes' page 1200 also displays notes 1202 created during previous sessions for viewing and sharing by the patron. Additionally, the 'notes' page 1200 may include a 'new note' UI control 1204 for creating a new note. More will be said about this functionality herein below. In addition to being viewed by the patron in the patron dashboard, notes 1202 may be created and viewed by an Instructor from the Instructor dashboard 302. It will be readily understood by those of ordinary skill that the notes may be stored in a database located one or both of locally and remotely. The stored notes may then be retrieved for viewing in any of the Instructor dashboard 302, the Patron dashboard 306 and the Session planner 308. More will be said about the Session planner 304 herein below.

Figure 13:
FIG. 13 provides a screenshot of creation of a new note in the 'Notes' page in a 'Patron Dashboard' from the GUI of FIG. 4.

Turning now to FIG. 13, shown is an 'add note' feature from the Notes page 1200. In embodiments, activation of the 'New note' UI control 1204 may launch a "New Note' form 1300 for creating a new note. In embodiments the "New Note' form may constitute a box for accepting text entered by a user via an input device such as a keyboard or a microphone. In embodiments, the text is easily edited by means of conventional keyboard commands or spoken commands. The form 1300 may include an 'Add' control 1302, activation of which saves the content entered on the form 1300 to the notes database. In embodiments, the form 1300 may also include a 'cancel' control 1304, by which the form 1300 is closed without the content being saved.

FIGS. 14-22 provide views of the pages of a session planner 304 within the user interface 300. In embodiments, an instructor may first select the patron 1404 for which a session is being planned. However, the UI also allows the Instructor to proceed with a session design without having selected a patron.

In embodiments, the UI flow may be from left to right, reflecting the conventional workflow in the western hemisphere in countries using the Roman alphabet. A series of UI controls 1412, 1420, 1418 is provided which filter the list of six hundred Pilates exercises. A first series of controls 1412 filters the list of exercises according to apparatus. A second series of controls 1420 filters the exercises according to difficulty. A third set of controls 1418 toggles between Classical and Modern exercises. While an instructor user may prefer to deploy the filters in a particular order, for example, apparatus-difficulty-classical/modern, it will be apparent that the instructor's goal for the session and personal preference may determine the order in which the filters are deployed. In fact, it is possible that the instructor may choose not to deploy one or more of the filters at all. For example, the instructor may wish to view all the exercises of a certain level of difficulty, in which case, the instructor may deploy the filter specifying the desired level of difficulty, without deploying any of the other filters. Or an instructor may wish to display all of the exercise that can be done with a particular piece of equipment, in which case, he/she would deploy only the filter for the specific piece of equipment.

When the instructor has finished narrowing the exercise list with the filters, the remaining exercises may be grouped in sequences according to Pilates convention. At any time during the generation of a filtered list, the instructor may add exercises to a session by dragging and dropping them from the list 1414 to a Session worksheet 1416. In embodiments, the instructor may alternatively select exercises by tapping them in the list 1414 which automatically adds them to the Session worksheet 1416.

By using the filters, flowing from left to right and back again, an instructor may create custom sequences of exercises for each patron; and may do so much more efficiently and expansively than when using pencil and paper. Embedded within every exercise, hidden from the eye, is that exercise's specific 96-point binary string.

In embodiments, the icons 1412 may represent common items of Pilates equipment as follows:
Floor mat 1422;
Power ring 1424;
Reformer 1426;
Wunda chair 1428;
Barrel 1430;
Cadillac 1432; and
Pulley 1434.

The Session page 1400 may also include a search feature 1408 for doing a text search of the list of exercises.

Additionally, the Session page 1400 may include session information 1406, such as time and date of the session and a prescribed repetition interval.

The session form 1400 may also include a session title 1402 and the name of the patron 1404 for whom the session is designed.

Figure 15:
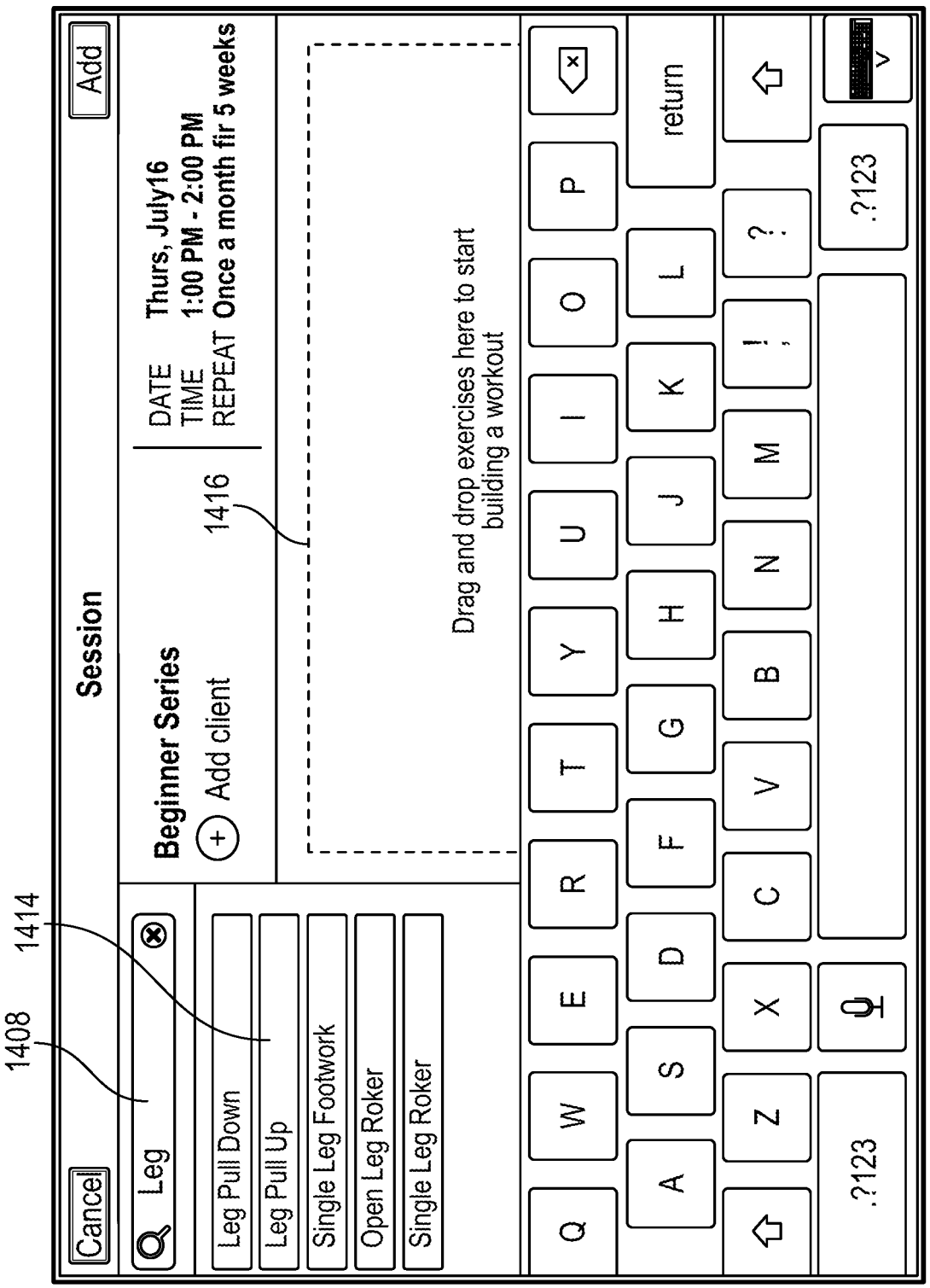
FIG. 15 provides a screenshot of a 'Search' page in a 'Session Builder' from the GUI of FIG. 4.

FIG. 15 shows an alternate method for filtering exercises. Here, the instructor has entered a text search using the search feature 1408, entering the key word "leg." The software returns a list of all Pilates exercise that include the key word in their names and/or descriptions. The instructor may then transfer the desired exercises to the worksheet 1416 as previously described.

Figure 16:
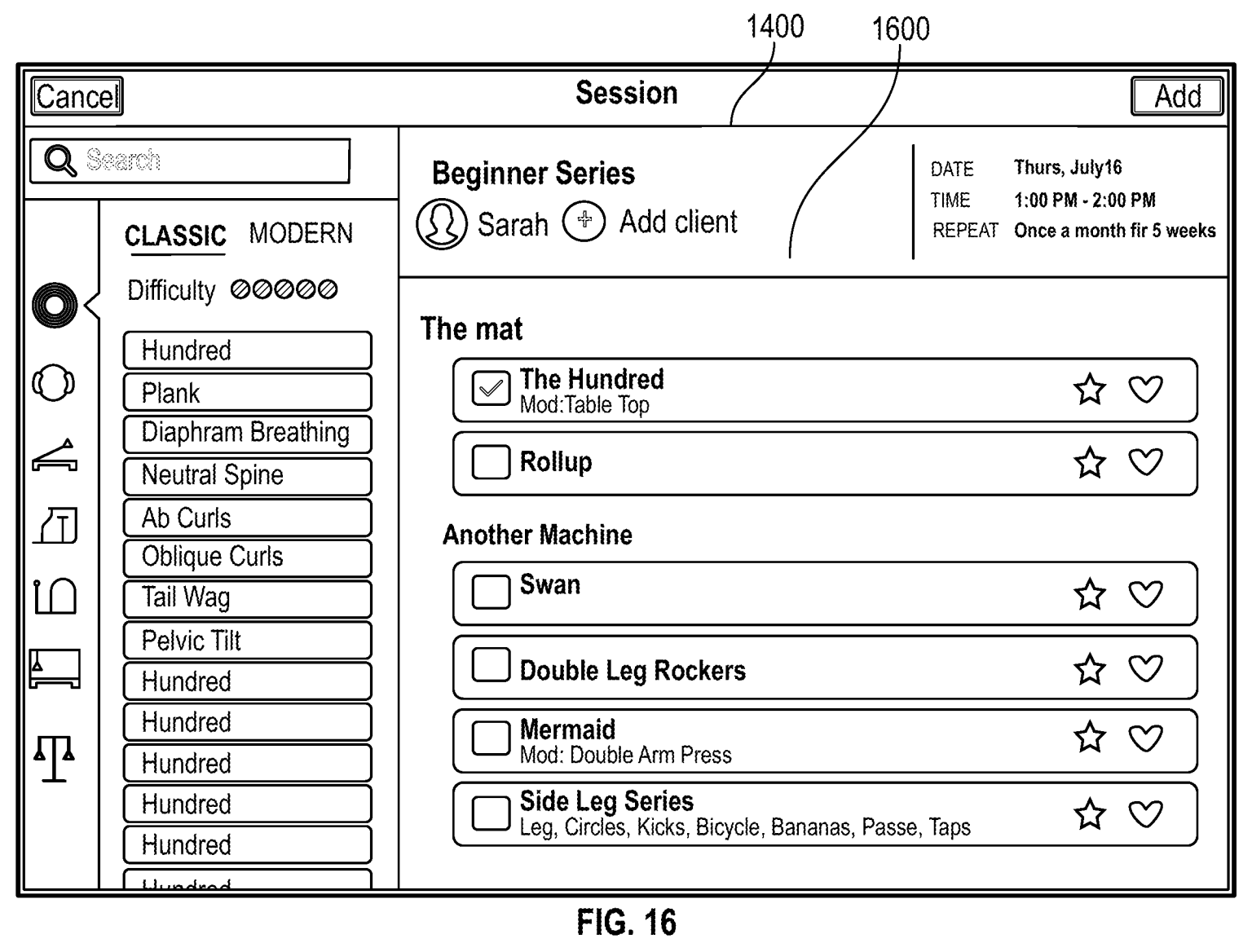

In an embodiment, when the instructor begins a session with the patron, the session will have already been organized and is displayed 1600 in the studio on a tablet or other computing device as shown in FIG. 16. At the end of the session, the instructor and patron may review the session, adding or removing exercises as needed, based on the patron's goals and the patron response to the just-completed session. Once accuracy is verified, the session may be saved by activating an 'ENTER' button.

Figure 17:
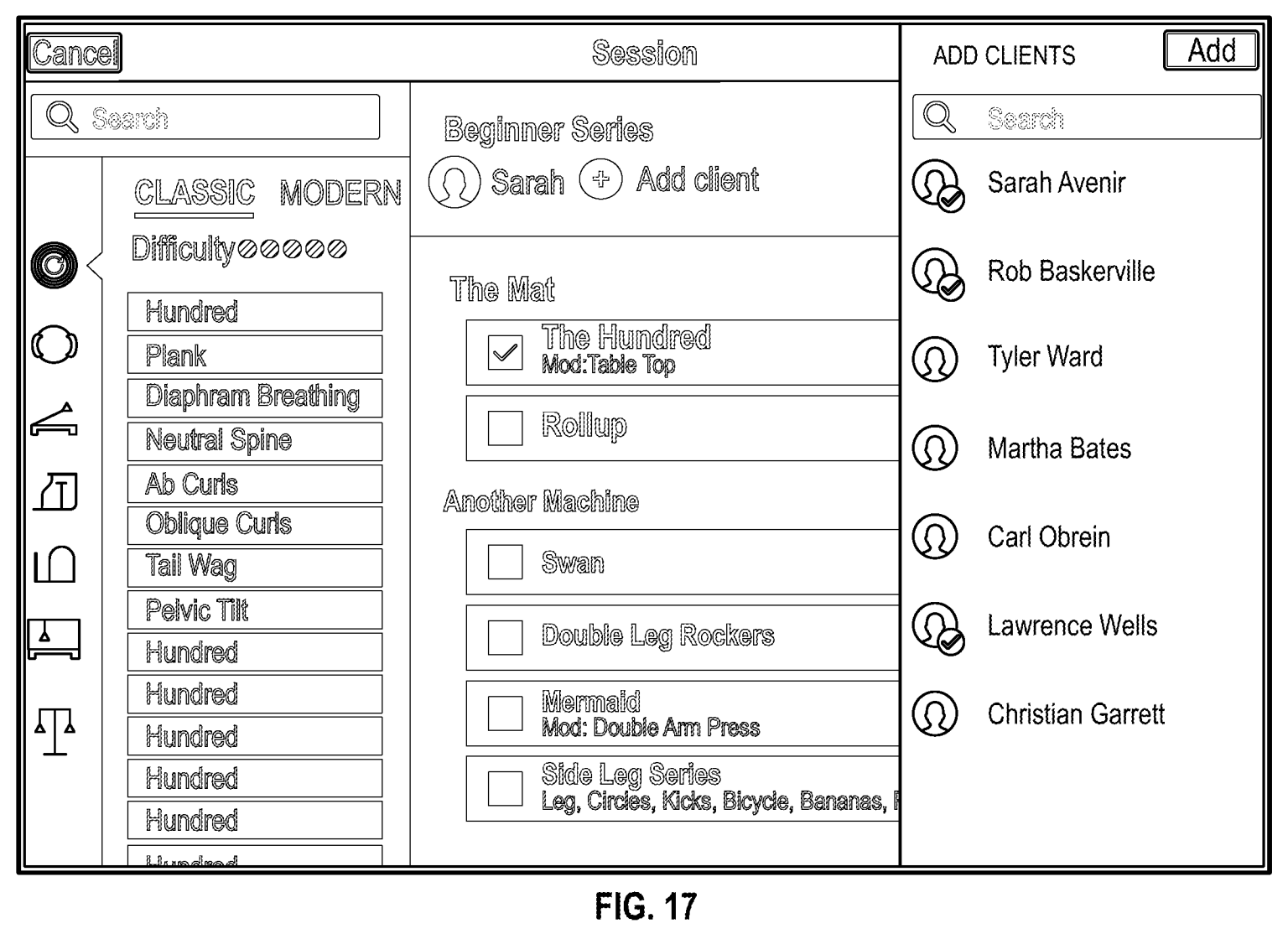

As shown in FIG. 17, patrons may be added to a session. There may be a number of occasions in which it is useful for an instructor to include a number of patrons on a single session. It is very common for two patrons to share a session with a single instructor to defray the cost of the session. In such a case, it would be desirable for the instructor to add both patrons to the session.

In another case, the session may have been designed for a class of several patrons. Thus, it would be useful to add all of the class members to the session.

Additionally, there may be several individual patrons who are all using the same session, for example all patrons who are at the beginner level, even though the instructor is working with them individually. Again, in such a case, it would ease recordkeeping for the Instructor to include all patrons using the session on the one session. To add a client, the instructor may do a name search using the search function and select the patrons to be added from a list, and add them by activating the 'Add client' control.

Figure 18:
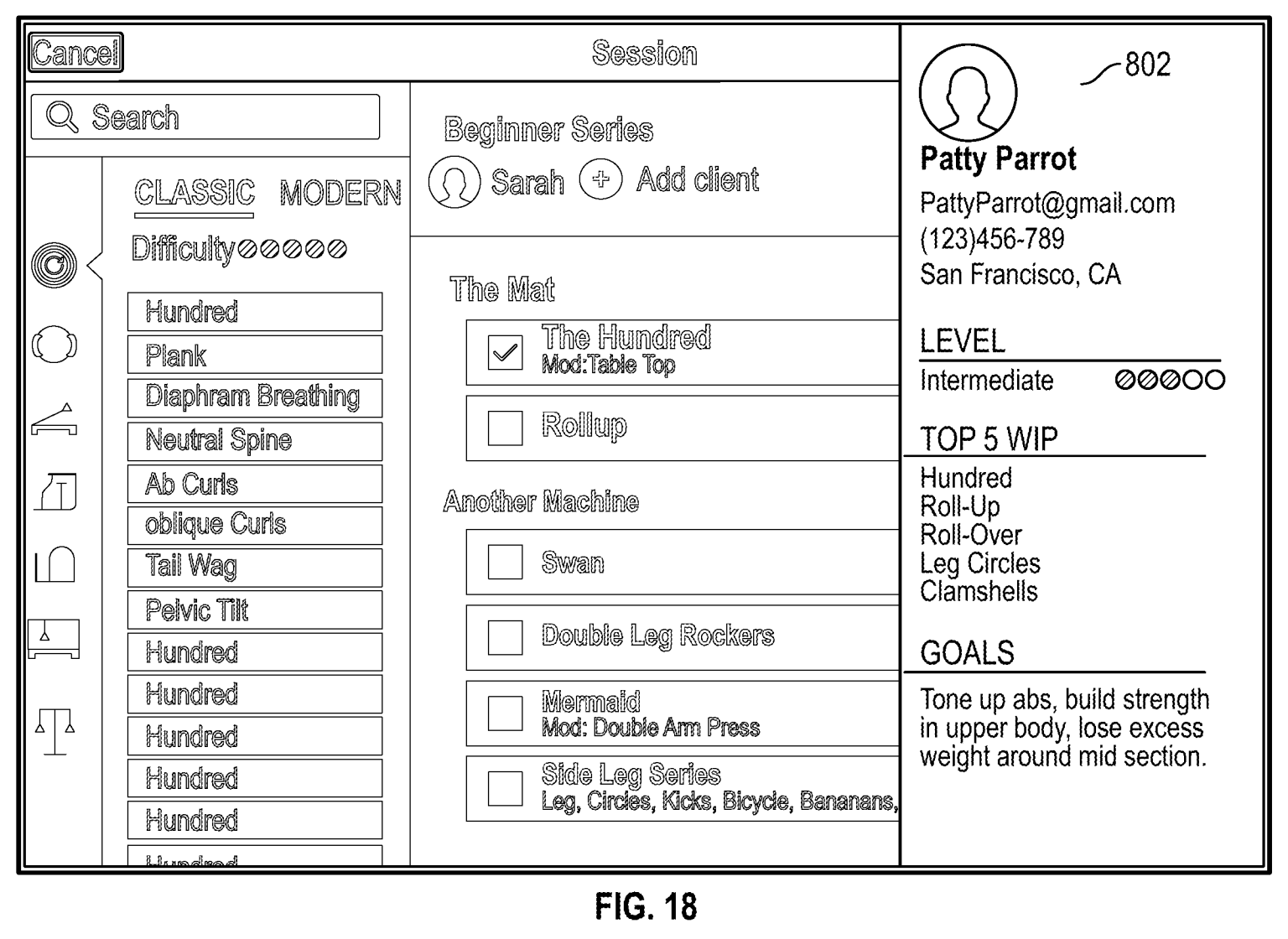

As shown in FIG. 18, patron information 802 may be accessed from within the session 1400.

Figure 19:
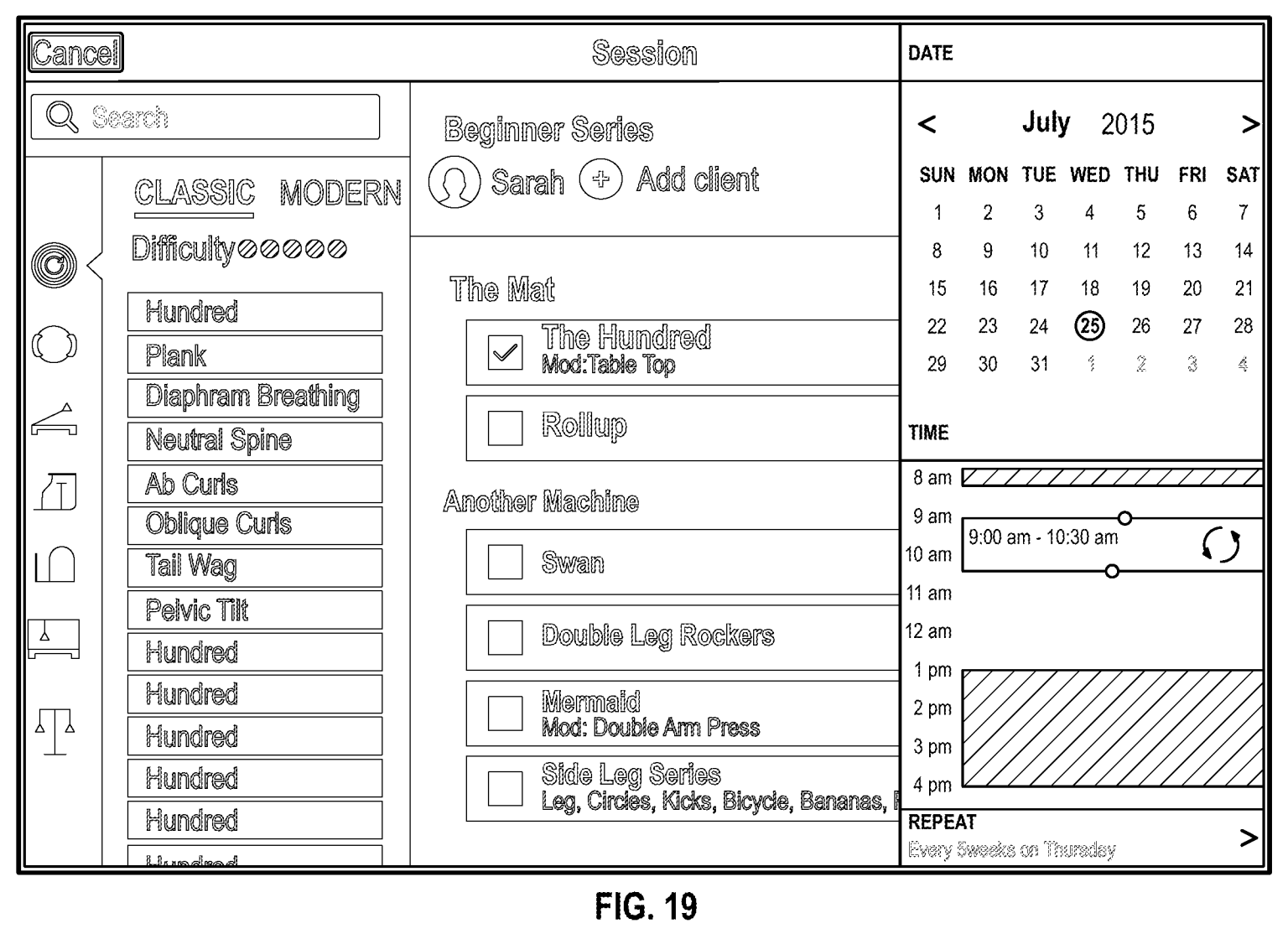

As shown in FIG. 19, the session 1400 may also display a session calendar 1000.

Figure 20A:
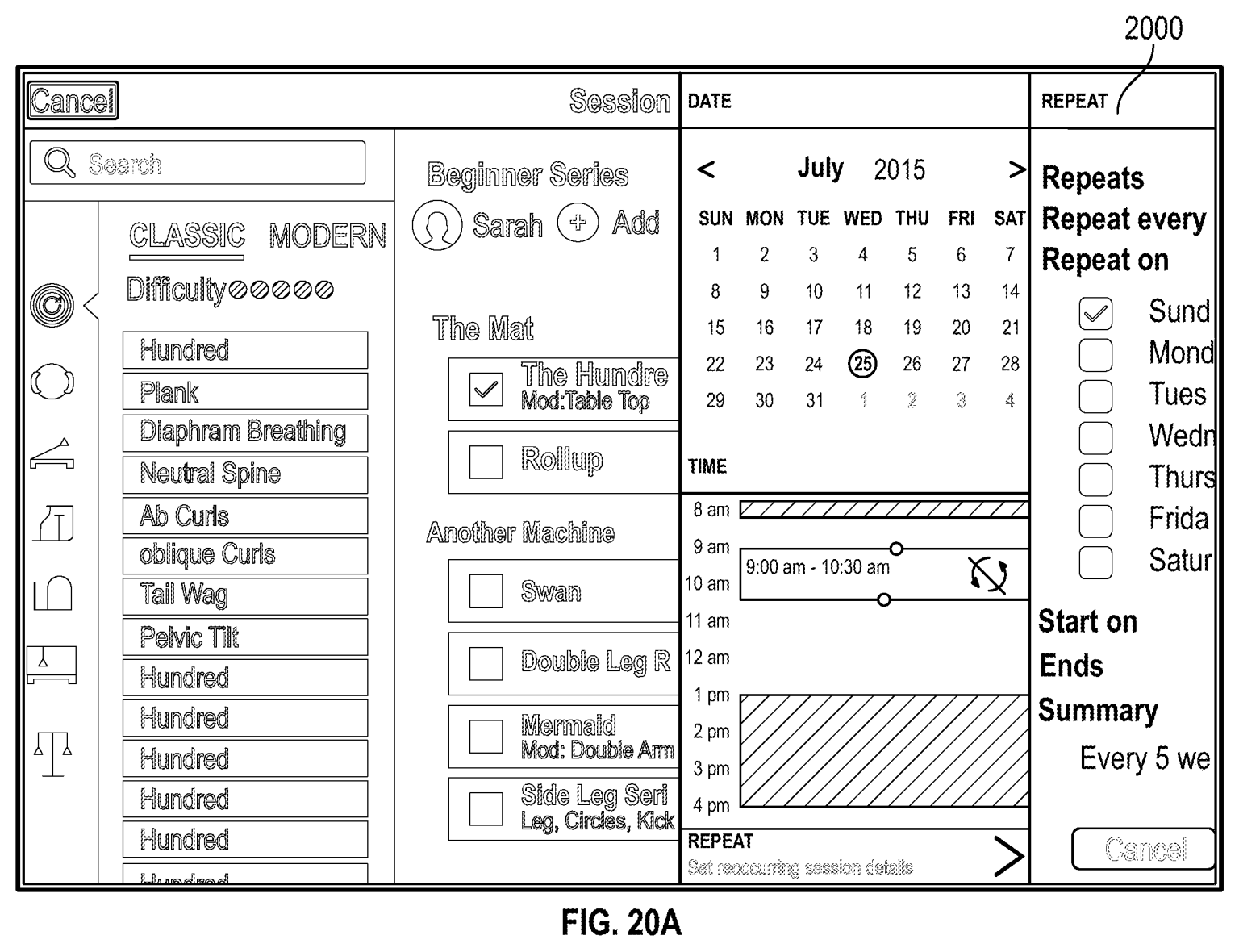
Figure 20B:
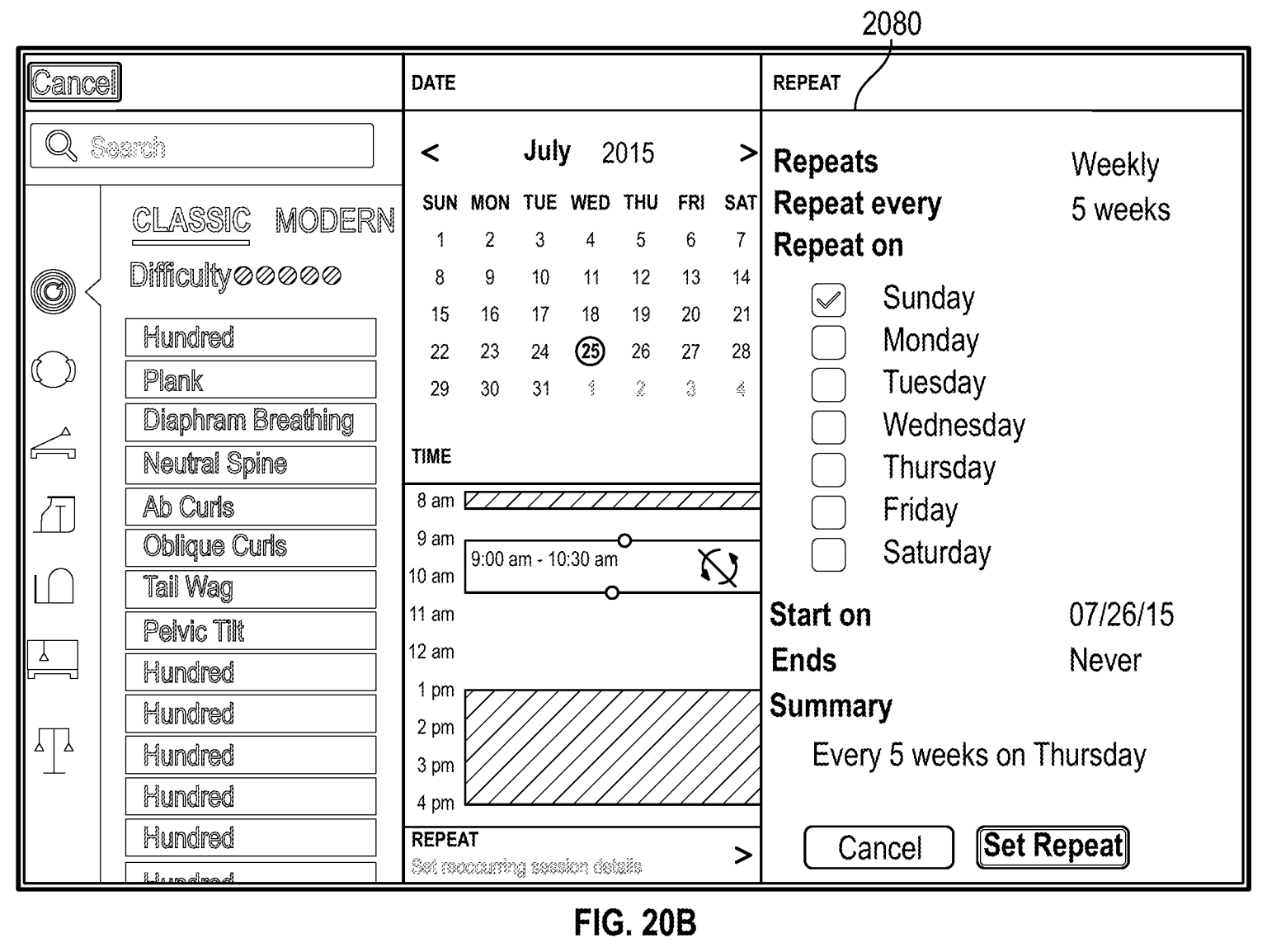
Figure 20C:
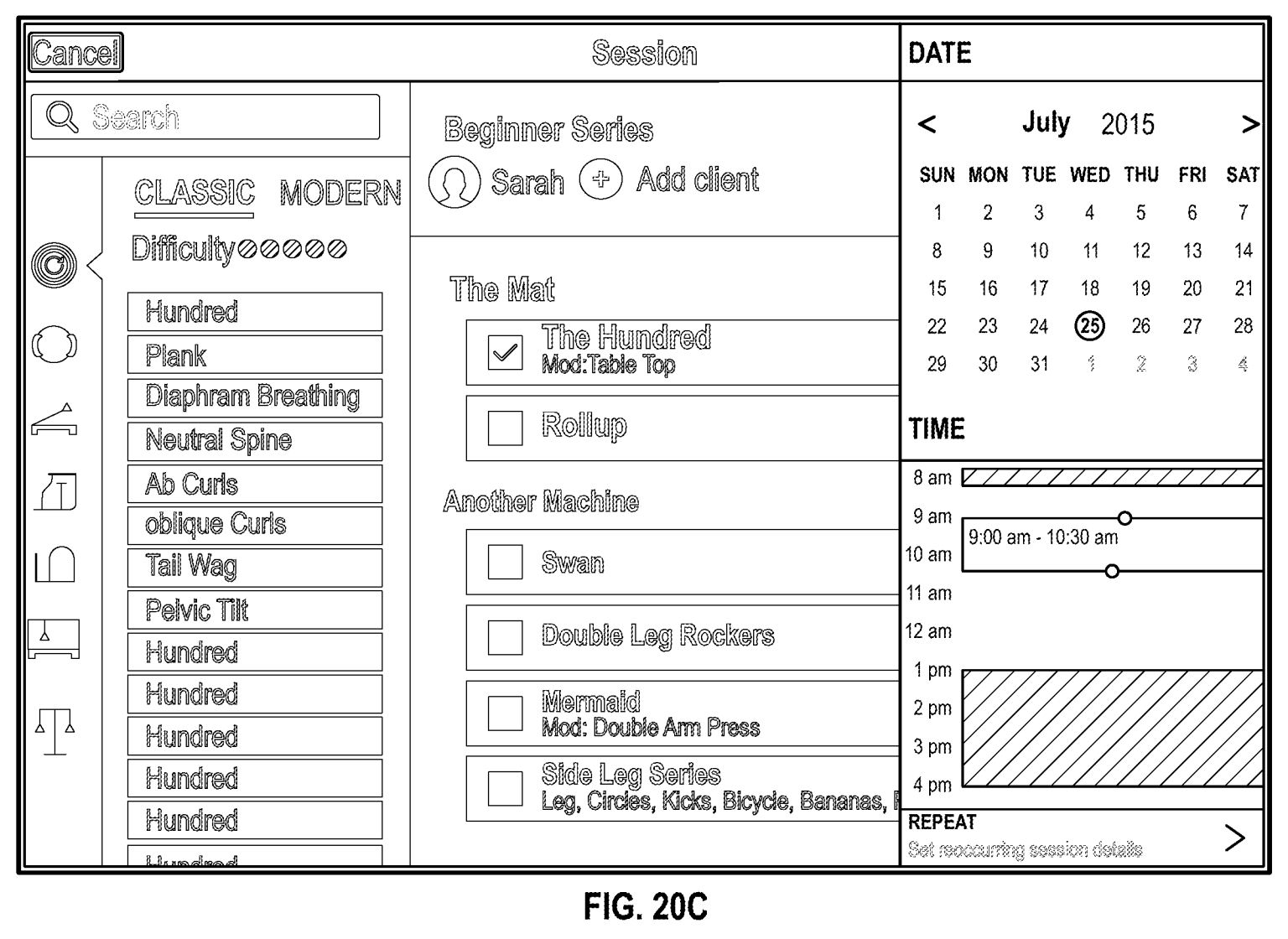

As shown in FIGS. 20A-C, instructions for repeating the session 1400 may be configured from within the session.

Figure 21:
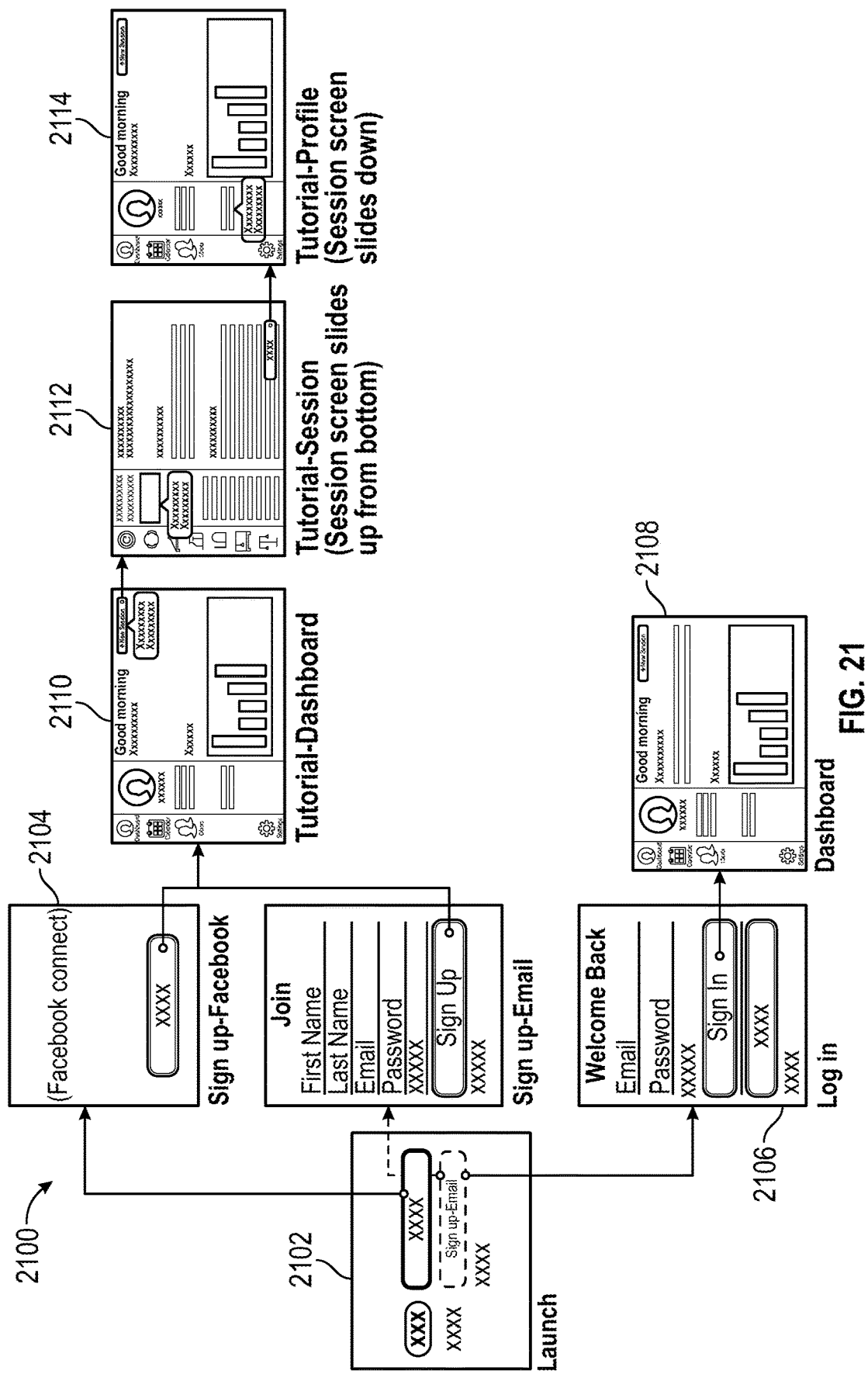
Figure 22:
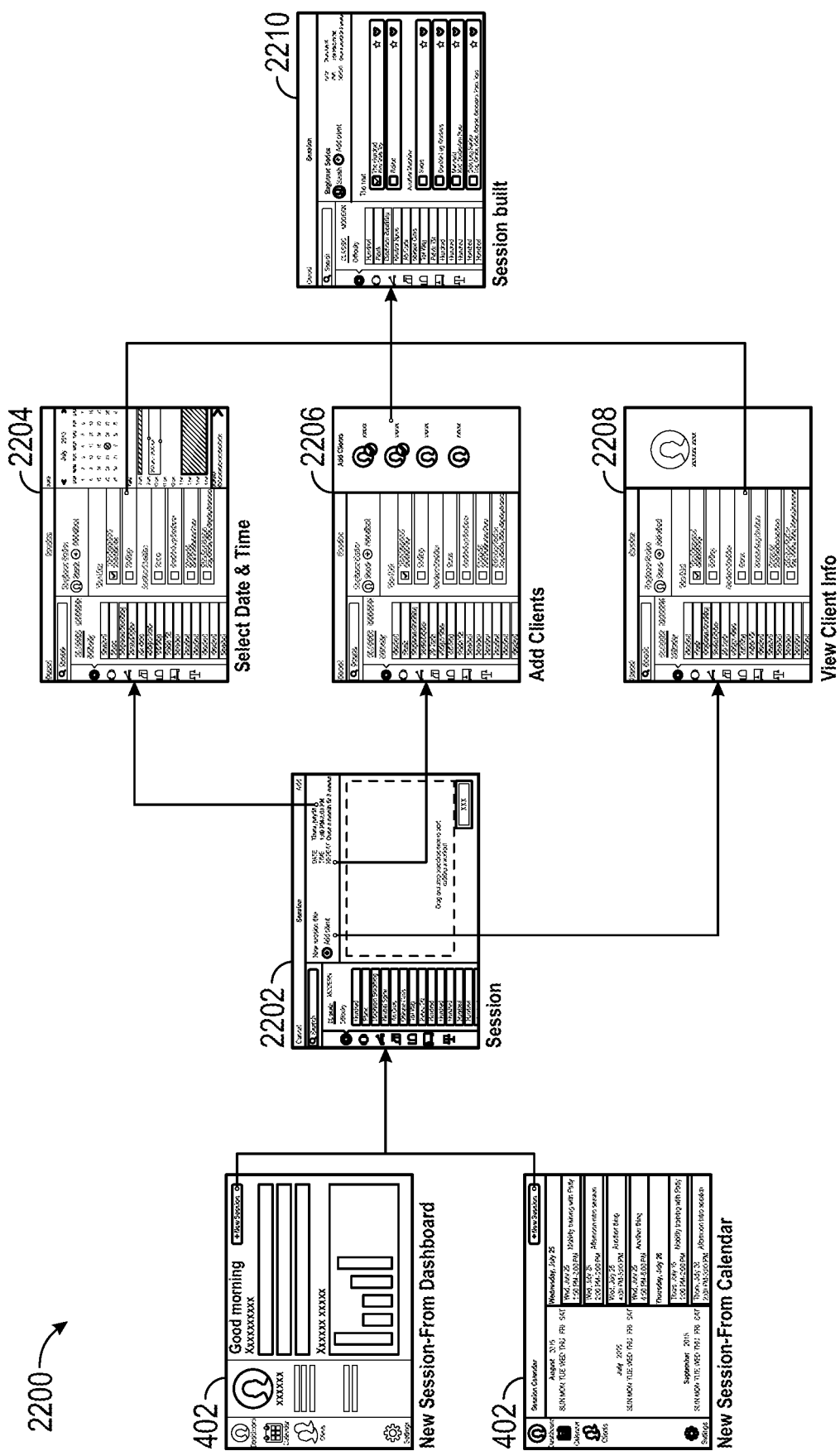

FIGS. 21-23 provide diagrams of some exemplary user flows relating to the user interface/application 300.

FIG. 21 is a diagram of a flow after the application 300 is launched:
Launch the applications 2102. When the application is first launched, the user may be given the option creating an account 2104 or logging in 2106, if there already exists an account for the user. These operations apply equally to instructor users and patron users;
When creating a new account 2104, the user may be given the option of authenticating through a social media account such as Facebook or LinkedIn. Alternatively, the user may provide an email to create an entirely new user account.

Having completed the 'sign up; 2104, the new user may be presented with a tutorial. For example, the user may first be shown a tutorial for using the Dashboard 2110;

The user may then be presented with a tutorial for working with the Session Planner;

The user may then be presented with a tutorial for working with the Profile;

A user who indicates at 2102 that he/she is a returning user may then be presented with a login screen 2106; and After completing the login, he/she may be presented with his/her Dashboard, either an Instructor Dashboard or a Patron Dashboard.

Figure 14:
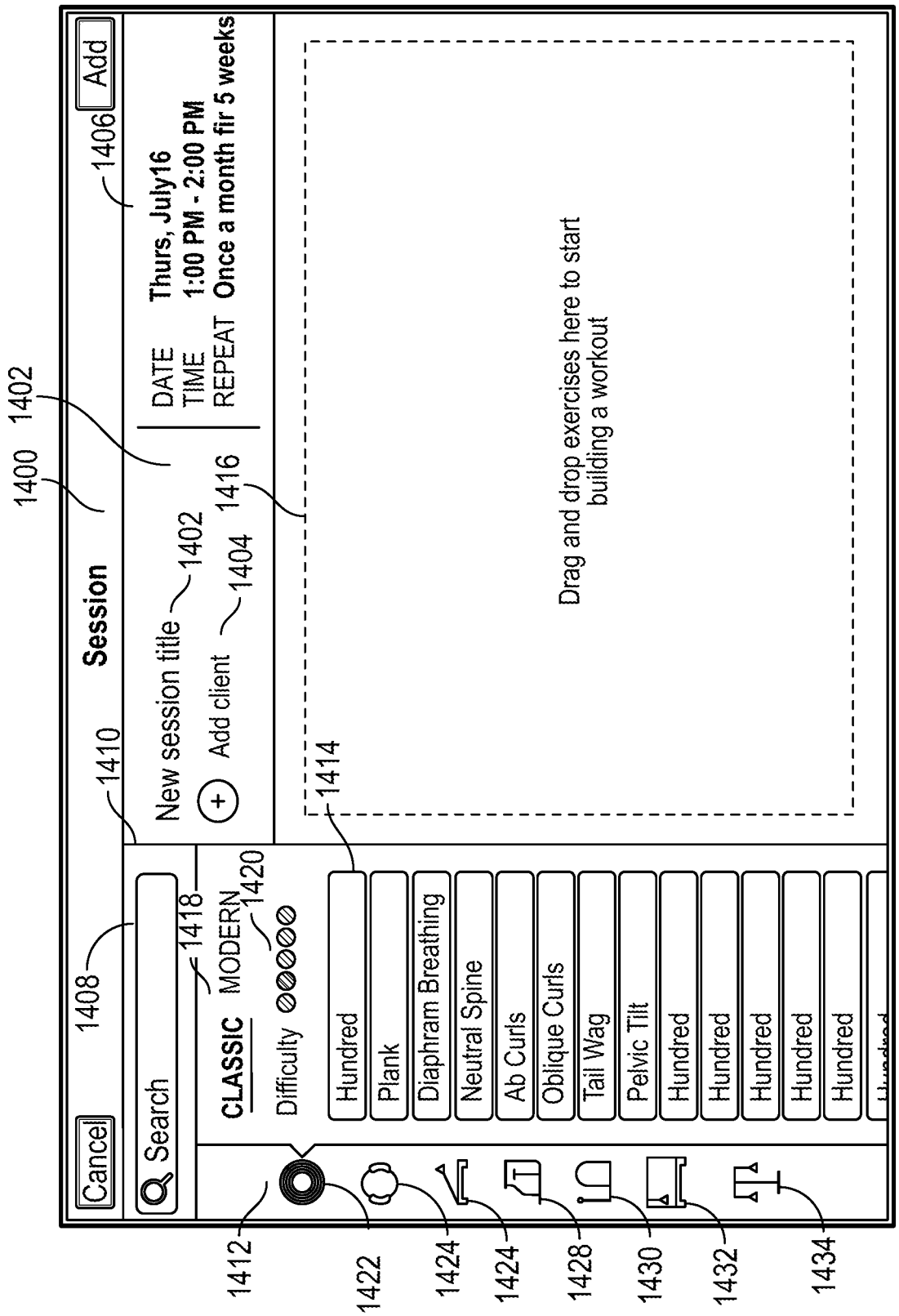
FIG. 14 provides a screenshot of a blank page in a 'Session Builder' from the GUI of FIG. 4.

FIG. 22 is a diagram of a flow for building a new session:

An Instructor/user may activate a 'new session' control 402 from either the instructor dashboard page (FIG. 4) or from the session calendar page (FIG. 5);

Activation of the 'new session' control 402 launches a new session (FIG. 14);

The user then builds the new session by setting the date and time of the session 2204; or Adding patrons to the session 2206;

After adding one or more patrons, the UI reveals the patront information for the newly added patron 2206; which results in:

the session being built 2210.

After the session is built, the user may apply filters to the exercise list as described to generate a list of exercises to be added to the session.

FIG. 23 is a diagram of a flow for adding patrons and working with patron information:

From the 'Patrons' page (FIG. 6) the Instructor/user may either add a new patron 2304 or view patron information for an existing patron 2306;

Upon activation of an 'add patron' control 2304, the application generates a new patron profile 2304;

the Instructor/user then adds the patron information 2308 to the new profile and saves it;

upon selection of an existing patron from the 'patron' page, the application initially allow the instructor to peek at the patron's record 2306;

The instructor is then able to view the full dashboard 2310.

The monitor is extremely useful as a tool for instructors to track, chart and share their patrons' progress for motivation, development, retention and recruiting more business. It is also invaluable for education because teacher-trainers are able to monitor trainees remotely.

The monitor also provides value for studio owners, who can exercise quality control over their employees/instructors as the first-ever digital means of oversight.

In embodiments, the entire system may be cloud-based. The practitioner may share the graphs and charts with the patron. The patron can post it on social media. He or she may also share it with his/her health care provider. All data may be backed up in the cloud, with the resultant effect that the entire network of instructors and all of their patrons are pooling their collective data in the cloud. The data collection gives instructors a comprehensive view of clients, enabling smarter session planning and better results. The app improves customer service, conversion and retention. Thus, the system provides a technology to track, chart, and share client progress.

The method and system herein described will modernize the Pilates industry by introducing new software technology that can quantify progress for the individual patron and instructor while aggregating data for use by the health care community and third-party payers.

One aim of the system is to generate data for a network of movement practitioners, such as Pilates instructors, and to report best practices back to them, while improving point-of-care for various the various pre-existing conditions they may encounter among their clients. Additionally, the system herein described enables the creation of alliances and partnerships between various providers and interest groups within the Pilates industry because of the ready sharing and exchange of information permitted by users of the system. For, example the system enables a content and distribution partnership whereby the partner schools can input exercise content.

An additional advantage of the cloud-based system is that cloud-based analytics integrate health data for health insurance companies. Thus, a period of accumulating viable health data will arm the Pilates industry with the big data it needs to verify the work to the insurance companies and the medical community. As such, the subject technology enables exercise statistics to be aggregated and analyzed at any scale, from the individual to the entire industry. While the present disclosure describes these advantages in relation to the Pilates industry, the same advantages may be achieved by applying the same principles and practices herein described to the gathering of client/practitioner data in any movement discipline, such as weight-training, ballet, yoga, martial arts, and so on.

In embodiments, the data analytics help to identify cost-saving opportunities for healthcare insurance companies by aggregating long-range health data that helps to pinpoint preventative care efficiencies.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

The invention claimed is:

1. A system for tracking and assessing subject response to a program of physical exercises, all of which are uniquely represented by single strings of Boolean values, comprising:
 a monitor for tracking and assessing subject response to programmed physical training, the monitor comprising:
 a display;
 a processor; and
 at least one memory;
 the system further comprising a remote data store communicatively coupled to said monitor;
 the at least one memory having stored therein instructions executable by the processor for:
  implementing on said display a graphical user interface that includes a session planner for displaying a session, the session comprising a list of exercises filtered to a particular patron for a particular session;
 the at least one memory further having stored therein a listing of unique strings of Boolean variables of uniform length, each unique string representing a single exercise within a predetermined system of physical training, wherein each bit of the string represents a parameter of a parameterized description that completely describes the exercise;

the instructions executable by the processor further comprising executable instructions for:
receiving data representing user selections of exercises;
receiving a user input to save the session, whereupon the session is saved to the local data store to create a persistent record of the session;
creating a session summary comprising an aggregate of binary strings for the exercises included in the session;
displaying the session summary to at least one of the user and the patron, wherein the session summary displays aggregates of:
raw movement data for the patron's skeletal system, joints and muscles;
level of difficulty;
apparatus used; and
storing said session summary in at least one of the at least one memory and the remote repository for later reporting and analysis.

2. The system of claim 1, the user interface further comprising at least one of:
an instructor dashboard;
a patron dashboard;
a calendar; a client list; and
a 'settings' page.

3. The system of claim 1, the patron list comprising a list of patrons and patron information for each patron in said list of patrons.

4. The system of claim 1, wherein said patron information comprises, for each patron, at least one of:
personal biographical information;
demographics; and
history.

5. The system of claim 1, the executable code further comprising executable code for:
aggregating said patron data with other patron data; and
at least one of analyzing and reporting said patron data.

6. The system of claim 5, wherein, prior to storage, said patron information is sanitized of personal identifying information.

7. The system of claim 1, the session planner comprising:
at least one interface control for displaying a listing of exercises;
at least one filter, a filter comprising a user interface control that, upon activation by a user, filters a displayed list of exercises to display a subset of exercises, wherein activation of a predetermined sequence of filters generates a session.

8. The system of claim 1, wherein said programmed physical training comprises at least one preplanned session of Pilates, said at least one preplanned session of Pilates comprising a sequence of Pilates exercises customized to the subject for a single encounter between instructor and patron.

9. The system of claim 1, wherein the monitor comprises one of a wireless mobile device, a tablet computer, a laptop computer and a desktop computer.

10. The system of claim 1, wherein said remote data store resides on a remote server, said server being communicatively coupled to said monitor via one or both of a wired and a wireless connection.

11. The system of claim 1, wherein said aggregated data is provided to practitioners, health care providers and insurance carriers for study and analysis to determine efficacy of the programmed training.

12. The system of claim 1, wherein said aggregated data is provided to employers to assess movement habits of employees.

13. The system of claim 1, wherein said aggregated data is provided to lead-generation companies to generate leads for healthcare-related companies.

14. The system of claim 1, wherein said user interface includes advertising targeted to patrons.

15. A monitor for tracking and assessing subject response to a program of physical exercises, all of which are individually and uniquely represented by single strings of Boolean variables, the monitor comprising:
a display;
a processor; and
at least one memory;
the at least one memory having stored therein instructions executable by the processor for:
implementing on said display a graphical user interface (GUI) that includes at least one of:
a session planner for displaying a session, the session comprising a list of exercises filtered to a particular patron for a particular session;
an instructor dashboard; and
a patron dashboard;
the at least one memory further having stored therein a listing of unique strings of Boolean variables of uniform length, each unique string representing a single exercise within a predetermined system of physical training, wherein each bit of the string represents a parameter of a parameterized description that completely describes the exercise;
the instructions executable by the processor further comprising executable instructions for:
receiving data representing user selections of individual exercises;
receiving a user input to save the session, whereupon the session is saved to the local data store to create a persistent record of the session;
creating a session summary comprising an aggregate of binary strings for the exercises included in the session;
wherein the session summary displays aggregates of:
raw movement data for the patron's skeletal system, joints and muscles;
level of difficulty;
apparatus used;
displaying the session summary to at least one of the user and the patron; and
storing said session summary in at least one of the at least one memory and a remote repository for later reporting and analysis.

16. The monitor of claim 15, said GUI further comprising:
a calendar;
a client list; and
a 'settings' page.

17. The monitor of claim 15, said session planner further comprising:
at least one interface control for displaying a listing of exercises;
at least one filter, a filter comprising a user interface control that, upon activation by a user, filters a displayed list of exercises to display a subset of exercises, wherein activation of a predetermined sequence of filters generates a session.

18. The monitor of claim 15, wherein said monitor is communicatively coupled to a remote server via one or both of a wired and a wireless connection, wherein said remote data store resides on the remote server.

19. A computer-implemented method for tracking and assessing subject response to programmed physical training comprising:
- a computer storing a listing of unique strings of Boolean variables of uniform length, each unique string representing a single exercise within a predetermined system of physical training, wherein each bit of the string represents a parameter of a parameterized description that completely describes the exercise a listing of unique binary strings of uniform length, each unique string representing a single exercise within a predetermined system of physical training, wherein each bit of the string represents a parameter of a parameterized description that completely describes the exercise represented by the unique string;
- the computer implementing on a display a graphical user interface that includes a session planner for displaying a session, the session comprising a list of exercises filtered to a particular patron for a particular session;
- the computer receiving users' selections of exercises;
- the computer receiving a user input to save the session, whereupon the session is saved to a local data store to create a persistent record of the session;
- the computer creating a session summary comprising an aggregate of strings for the exercises included in the session;
    - wherein the session summary displays aggregates of:
        - raw movement data for the patron's skeletal system, joints and muscles;
        - level of difficulty;
        - apparatus used;
- the computer displaying the session summary to at least one of a user and a patron; and
- storing said session summary in at least one of a local data store and a remote data store.

20. A computer program product comprising at least one non-transitory computer-readable medium having computer-readable instructions embodied thereon, which when executed by a processor performs a method for tracking and assessing subject response to programmed physical training, the method comprising:
- storing a listing of unique strings of Boolean variable of uniform length, each unique string representing a single exercise within a predetermined system of physical training, wherein each bit of the string represents a parameter of a parameterized description that completely describes the exercise represented by the unique string;
- implementing on a display a graphical user interface that includes a session planner for displaying a session, the session comprising a list of exercises filtered to a particular patron for a particular session;
- receiving a user's selections of exercises;
    - receiving a user input to save the session, whereupon the session is saved to a local data store to create a persistent record of the session;
    - creating a session summary comprising an aggregate of binary strings for the exercises included in the session;
        - wherein the session summary displays aggregates of:
            - raw movement data for the patron's skeletal system, joints and muscles;
- level of difficulty;
- apparatus used;
- displaying the session summary to at least one of a user and a patron; and
- storing said session summary in at least one of a local data store and a remote data store.

* * * * *